United States Patent [19]
Wallace et al.

[11] Patent Number: 5,646,253
[45] Date of Patent: Jul. 8, 1997

[54] RECOMBINANT HUMAN ANTI-LK26 ANTIBODIES

[75] Inventors: Thomas Paul Wallace, Gight; William Joseph Harris, Carnoustie; Francis Joseph Carr, Balmedie, all of Great Britain; Wolfgang J. Rettig; Pilar Garin-Chesa, both of Biberach, Germany; Lloyd J. Old, New York, N.Y.

[73] Assignees: Memorial Sloan-Kettering Cancer Center, New York, N.Y.; Scotgen Biopharmaceuticals, Inc., Menlo Park, Calif.

[21] Appl. No.: 207,996

[22] Filed: Mar. 8, 1994

[51] Int. Cl.$^6$ .................................................. C07K 16/46
[52] U.S. Cl. .................. 530/387.3; 530/324; 530/391.1; 530/388.8; 530/388.85
[58] Field of Search .......................... 530/391.1, 387.3, 530/388.8, 388.83, 324

[56] References Cited

U.S. PATENT DOCUMENTS

| | | | |
|---|---|---|---|
| H1312 | 5/1994 | Coughlin et al. | 530/331 |
| 4,851,332 | 7/1989 | Rettig et al. | 435/7.1 |
| 5,225,539 | 7/1993 | Winter | 530/387.3 |

FOREIGN PATENT DOCUMENTS

| | | |
|---|---|---|
| 197435 | 10/1986 | European Pat. Off. |
| 92/04381 | 3/1992 | WIPO |

OTHER PUBLICATIONS

Carter, P. et al. "Humanization of an anti-p185$^{HER2}$ antibody for human cancer therapy". *Proceedings of the National Academy of Sciences, USA*, 89:4285–4289 (1992).

Gorman, S.D. et al. "Reshaping a therapeutic CD4 antibody". *Proceedings of the National Academy of Sciences, USA* 88:4181–4185 (1991).

Ohtomo, T. et al. "Humanization of Mouse ONS-M21 Antibody with the Aid of Hybrid Variable Regions". *Molecular Immunology* 32(6):407–416 (1995).

Queen, C. et al. "A humanized antibody that binds to the interleukin 2 receptor". *Proceedings of the National Academy of Sciences, USA* 86:10029–10033 (1989).

Riechmann, L. et al. "Reshaping human antibodies for therapy". *Nature* 332:323–327 (1988).

Roguska, M. et al. "Humanization of murine monoclonal antibodies through variable domain resurfacing". *Proceedings of the National Academy of Sciences, USA* 91:969–973 (1994).

Routledge, E. et al. "A humanized monovalent CD3 antibody which can activate homologous complement". *European Journal of Immunology* 21:2717–2725 (1991).

Schumacher, C.L. et al. "Use of Mouse Anti–Rabies Monoclonal Antibodies in Postexposure Treatment of Rabies". *Journal of Clinical Investigation* 84:971–075 (1989).

Studnick, G. et al. "Human–engineered monoclonal antibodies retain full specific binding activity by preserving non–CDR complementarity–modulating residues". *Protein Engineering* 7(6):805–814 (1994).

Tempest, P. et al. "Reshaping a Human Monoclonal Antibody to Inhibit Human Respiratory Syncytial Virus Infection In Vivo". *Bio/Technology* 9:266–271 (1991).

Verhoeyen, M. et al. "Reshaping Human Antibodies: Grafting an Antilysozyme Activity". *Science* 239:1534–1536 (1988).

*Primary Examiner*—Frank C. Eisenschenk
*Attorney, Agent, or Firm*—Felfe & Lynch

[57] ABSTRACT

The invention provides for the production of several humanized murine antibodies specific for the antigen LK26, which is recognized by the murine antibody LK26. This antigen is expressed on all choriocarcinoma, teratocarcinoma and renal cancer cell lines whereas it is not expressed on cell lines of leukaemias, lymphomas, neuroectodermally-derived and epithelial tumour cell lines (excepting a small subset of epithelial cell lines). Furthermore, whereas renal cancer cell lines express the LK26 antigen, normal renal epithelial cells do not. Similarly, with the exception of the trophoblast, all normal adult and fetal tissues tested are negative for the LK26 phenotype. The invention also provides for numerous polynucleotide encoding humanized LK26 specific antibodies, expression vectors for producing humanized LK26 specific antibodies, and host cells for the recombinant production of the humanized antibodies. The invention also provides methods for detecting cancerous cells (in vitro and in vivo) using humanized LK26 specific antibodies. Additionally, the invention provides methods of treating cancer using LK26 specific antibodies.

2 Claims, 14 Drawing Sheets

```
    CAGGTSMARCTGCAGSAGTCWGGGGGAGACTTGGTGAAGCCTGGAGGGTC
    ----.----+----.----+----.----+----.----+----.----+   50
    GTCCASKTYGACGTCSTCAGWCCCCCTCTGAACCACTTCGGACCTCCCAG q   v  k/q  l   q  e/q  s   g   g   d   l   v   k   p   g   g   s

----.----+----.----+----.----+----.----+----.----+

CCTGAAACTCTCCTGTGCAGCCTCTGGATTCACTTTCAGT GGCTATGGCT
    ----.----+----.----+----.----+----.----+----.----+  100
    GGACTTTGAGAGGACACGTCGGAGACCTAAGTGAAAGTCA CCGATACCGA l   k   l   s   c   a   a   s   g   f   t   f   s  |g   y   g   l

----.----+----.----+----.----+----.----+----.----+

TGTCT TGGGTTCGCCAGACTCCAGACAAGAGGCTGGAGTGGGTCGCA ATG
    ----.----+----.----+----.----+----.----+----.----+  150
    ACAGA ACCCAAGCGGTCTGAGGTCTGTTCTCCGACCTCACCCAGCGT TAC s  |w   v   r   q   t   p   d   k   r   l   e   w   v   a  |n

----.----+----.----+----.----+----.----+----.----+

ATTAGTAGTGGTGGTAGTTATACCTACTATGCAGACAGTGTGAAGGGG CG
    ----.----+----.----+----.----+----.----+----.----+  200
    TAATCATCACCACCATCAATATGGATGATACGTCTGTCACACTTCCCC GC i   s   s   g   g   s   y   t   y   y   a   d   s   v   k   g |r

----.----+----.----+----.----+----.----+----.----+

ATTCGCCATCTCCAGAGACAATGCCAAGAACTCCCTGTTCCTGCAAATGA
    ----.----+----.----+----.----+----.----+----.----+  250
    TAAGCGGTAGAGGTCTCTGTTACGGTTCTTGAGGGACAAGGACGTTTACT f   a   i   s   r   d   n   a   k   n   s   l   f   l   q   m   s

```
GCAGTCTGAAGTCTGACGACACAGCCATTTATATCTGTGCAAGACATGGG
----.----+----.----+----.----+----.----+----.----+  300
CGTCAGACTTCAGACTGCTGTGTCGGTAAATATAGACACGTTCTGTACCC s  l  k  s  d  d  t  a  i  y  i  c  a  r  n  g

----.----+----.----+----.----+----.----+----.----+

GACGATCCCGCCTGGTTTGCTTACTGGGGCCAAGGGACTCTAGTCACTGT
----.----+----.----+----.----+----.----+----.----+  350
CTGCTAGGGCGGACCAAACGAATGACCCCGGTTCCCTGAGATCAGTGACA d  d  p  a  w  f  a  y  w  g  q  g  t  l  v  t  v

----.----+----.----+----.----+----.----+----.----+

CTCTGCT
----.---+ 357
GAGACGA s  a

```
GACATTGAGCTCACCCAGTCTCCAGCACTCATGGCTGCATCTCCAGGGGA
----.----+----.----+----.----+----.----+----.----+   50
CTGTAACTCGAGTGGGTCAGAGGTCGTGAGTACCGACGTAGAGGTCCCCT d   i   e   l   t   q   s   p   a   l   n   a   a   s   p   g   e
_____

----.----+----.----+----.----+----.----+----.----+

GAAGGTCACCATCACCTGCAGTGTCAGCTCAAGTATAAGTTCCAACAACT
----.----+----.----+----.----+----.----+----.----+   100
CTTCCAGTGGTAGTGGACGTCACAGTCGAGTTCATATTCAAGGTTGTTGA k   v   t   i   t   c   s   v   s   s   s   i   s   s   n   n   l

----.----+----.----+----.----+----.----+----.----+

TGCACTGGTACCAGCAGAAGTCAGAAACCTCCCCCAAACCCTGGATTTAT
----.----+----.----+----.----+----.----+----.----+   150
ACGTGACCATGGTCGTCTTCAGTCTTTGGAGGGGGTTTGGGACCTAAATA h   w   y   q   q   k   s   e   t   s   p   k   p   w   i   y

----.----+----.----+----.----+----.----+----.----+

GGCACATCCAACCTGGCTTCTGGAGTCCCTCTTCGCTTCAGAGGCTTTGG
----.----+----.----+----.----+----.----+----.----+   200
CCGTGTAGGTTGGACCGAAGACCTCAGGGAGAAGCGAAGTCTCCGAAACC g   t   s   n   l   a   s   g   v   p   l   r   f   r   g   f   g

----.----+----.----+----.----+----.----+----.----+

ATCTGGGACCTCTTATTCTCTCACAATCAGCAGCATGGAGGCTGAAGATG
----.----+----.----+----.----+----.----+----.----+   250
TAGACCCTGGAGAATAAGAGAGTGTTAGTCGTCGTACCTCCGACTTCTAC s   g   t   s   y   s   l   t   i   s   s   n   e   a   e   d   a

```
CTGCCACTTATTACTGT CAACAGTGGAGTAGTTACCCGTACATGTACACG
----.----+----.----+----.----+----.----+----.----+----.----+  300
GACGGTGAATAATGACA GTTGTCACCTCATCAATGGGCATGTACATGTGC a   t   y   y   c   q   q   w   s   s   y   p   y   m   y   t

----.----+----.----+----.----+----.----+----.----+----.----+

TTCGGAGGGGGGACCAAGTTGGAAATAAAA
----.----+----.----+----.----+  330
AAGCCTCCCCCCTGGTTCAACCTTTATTTT f   g   g   g   t   k   l   e   i   k

RECOMBINANT HUMAN ANTI-LK26 ANTIBODIES

1. FIELD OF THE INVENTION

The present invention is related to the field of molecular biology, and more particularly to humanized antibodies.

2. BACKGROUND

The present invention provides novel recombinant immunoglobulins specific for the human LK26 cancer antigen, polynucleotides encoding the novel immunoglobulins, and host cells containing the novel polynucleotides. The invention also provides methods for the production of these recombinant antibodies, for the diagnosis and treatment of certain human cancers.

Transformation of a normal cell to a malignant cell is often accompanied by a change in the expression of cell surface antigens. These changes in the cell surface can be detected using monoclonal antibodies specific for such antigens. In this way, different cancer cells can be detected and characterized (Lloyd, K. O. (1983) "Human Tumour Antigens: Detection and Characterization with Monoclonal Antibodies" in R. B. Herberman, ed., Basic and Clinical Tumour Immunology, pp 159–214, Martinus Nijhoff, Boston).

European Patent Application Number 86104170.5 (Rettig) describes the generation and characterization of the murine monoclonal antibody 'LK26'. The antibody was generated by the application of the hybridoma technology of Kohler and Milstein (Kohler, G. and Milstein, C. (1975) Nature 256:495–497). The antibody specifically recognizes a cell surface glycoprotein of molecular weight between 30 and 35 kDa (the LK26 antigen). This antigen is expressed on all choriocarcinoma, teratocarcinoma and renal cancer cell lines whereas it is not expressed on cell lines of leukaemias, lymphomas, neuroectodermally-derived and epithelial tumour cell lines (excepting a small subset of epithelial cell lines). Furthermore, whereas renal cancer cell lines express the LK26 antigen, normal renal epithelial cells do not. Similarly, with the exception of the trophoblast, all normal adult and fetal tissues tested are negative for the LK26 phenotype.

The specificity of the LK26 murine antibody makes it a powerful tool for the detection and characterization of particular human cancer types in vitro. However, the in vivo use of murine antibodies as agents for the diagnosis and treatment of human diseases is severely curtailed by a number of factors. Specifically, the human body recognizes murine antibodies as foreign. This can elicit a human anti-mouse antibody (HAMA) response (Schroff, R. et al. (1985) Cancer Res. 45:879–885) which results in rapid clearance of the antibody from the circulation. Furthermore, the Fc portion of a murine antibody is not as efficacious as the human Fc at stimulating human complement or cell-mediated cytotoxicity. Therefore, it is desirable to circumvent these problems associated with the in vivo use of murine antibodies in diagnosis and therapy.

EP120694 (Celltech) and EP125023 (Genentech) disclose the development of 'chimeric' antibodies using recombinant DNA methods. Such antibodies comprise the variable regions from one species, e.g. mouse, and the constant regions from another species, e.g. human. Such chimeric antibodies have the advantage that they retain the specificity of the murine antibody but can also stimulate human Fc dependent complement fixation and cell-mediated cytotoxicity. However, the murine variable regions can still elicit a HAMA response (Bruggemann, M. et al. (1989) J. Exp. Med. 170:2153–2157) thereby limiting the value of chimeric antibodies as diagnostic and therapeutic agents.

British Patent Application Number GB2188638A (Winter) discloses a process whereby recombinant antibodies can be generated by substitution of only the variable region CDRs of one antibody with those from another. Typically, this 'CDR-grafting' technology has been applied to the generation of recombinant, pharmaceutical antibodies consisting of murine CDRs, human variable region frameworks and human constant regions (e.g. Riechmann, L. et al., (1988) Nature 332:323–327). Such 'reshaped' or 'humanized' antibodies have less murine content than chimeric antibodies and retain the human constant regions necessary for the stimulation of human Fc dependent effector functions. Consequently, humanized antibodies are less likely than chimeric antibodies to evoke a HAMA response when administered to humans, their half-life in circulation should approach that of natural human antibodies and their diagnostic and therapeutic value is enhanced.

In practice, simply substituting murine CDRs for human CDRs is not sufficient to generate efficacious humanized antibodies retaining the specificity of the original murine antibody. There is an additional requirement for the inclusion of a small number of critical murine antibody residues in the human variable region. The identity of these residues depends on the structure of both the original murine antibody and the acceptor human antibody. British Patent Application Number 9019812.8 describes a method for identifying a minimal number of substitutions of foreign residues sufficient to promote efficacious antigen binding.

The invention described herein provides a process for the inclusion of residues into the humanized antibodies which facilitates the proper association of the VH and VL domains and thereby antigen binding.

The present invention provides novel, humanized monoclonal antibodies specific for the human LK26 cancer antigen and various antibody derivatives comprising humanized variable regions that are specific for LK26. This has been achieved by the conversion of the murine LK26 monoclonal antibody described in European Patent Application Number 86104170.5 to humanized antibodies by utilizing CDR-grafting technologies. The invention also provides methods for the production of these humanized antibodies to be used in the diagnosis (both in vivo and in vitro) and treatment of certain human cancers. Prior to the work of the inventors, it was not known that the LK26 antibody or any other non-human antibody specific for the the LK26 antigen could be humanized so as to retain useful binding specificity.

3. BRIEF DESCRIPTION OF THE FIGURES

FIGS. 1a and 1b show the DNA sequence (SEQ ID NO:26) and corresponding amino acid sequence (SEQ ID NO:27) of the murine LK26 heavy chain variable region (VH). The CDRs are boxed. Underlined nucleotides and amino acid residues are derived from the oligonucleotide primers used. The backslash mark is used to indiacte the result obtained with the consensus primers.

FIGS. 2a and 2b show the DNA sequence (SEQ ID NO:28) and corresponding amino acid sequence (SEQ ID NO:29) of the murine LK26 light chain variable region (VK). The CDRs are boxed. Underlined nucleotides and amino acid residues are derived from the oligonucleotide primers used.

Figure 3:
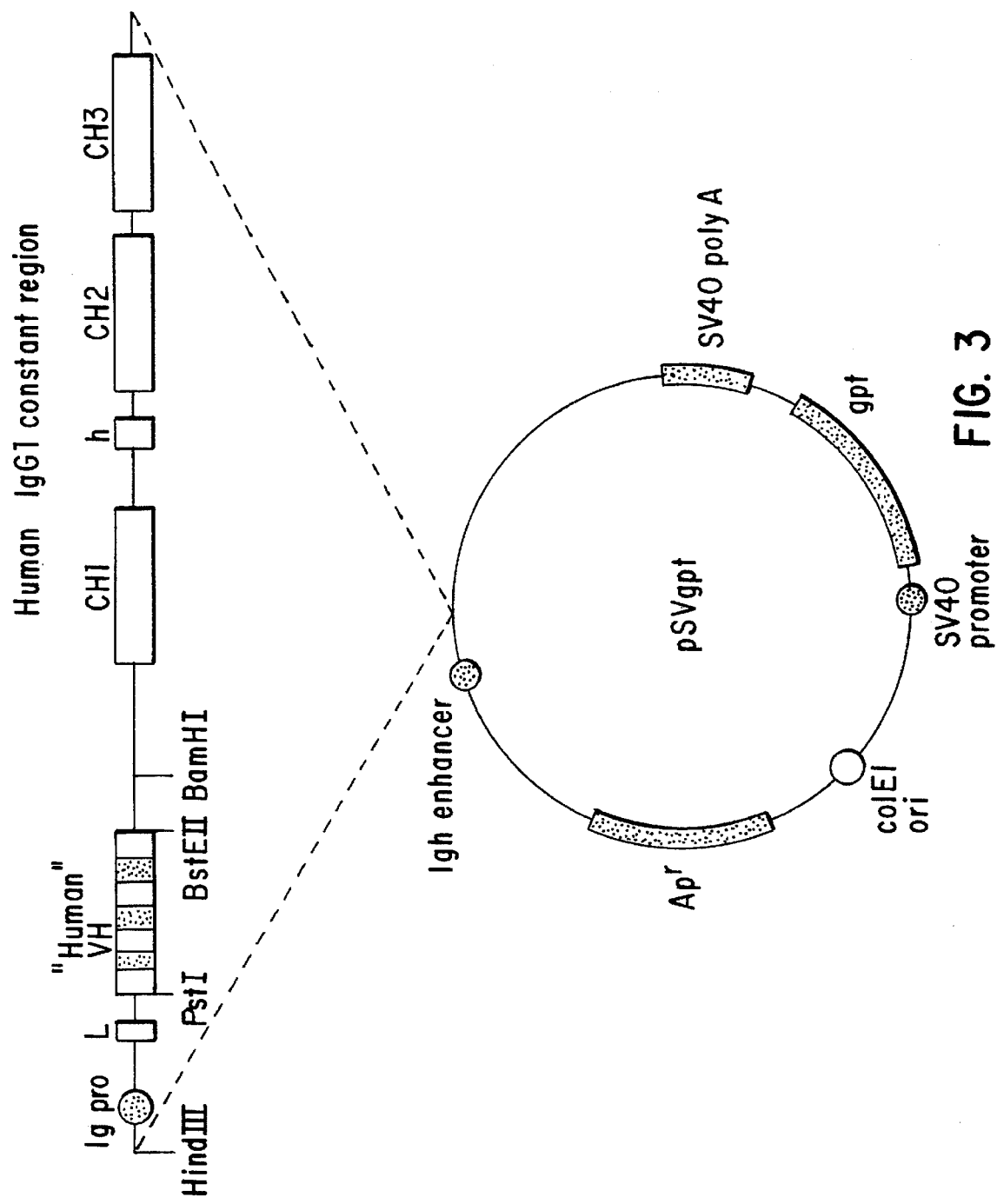
FIG. 3 shows the vector pSVgpt, which is used for the expression of chimeric or humanized heavy chains in mammalian cells.

FIG. 5–12 provide graphical data of ELISA results measuring the binding of different humanized LK26 antibodies.

4. SUMMARY OF THE INVENTION

One aspect of the invention is to provide humanized antibodies specific for the LK26 antigen.

Another aspect of the invention is to provide polynucleotides encoding humanized antibodies specific for the LK26 antigens. Various expression vectors comprising polynucleotides encoding humanized LK26 antibodies joined to promoter sequences are also provided. Similarly, another aspect of the invention is host cells transformed with expression vectors for the expression of humanized LK26 specific antibodies.

Another aspect of the invention is to provide humanized anti-LK26 antibodies that are labeled with a detectable label or a therapeutic label.

Another aspect of the invention is to provide methods for treating and/or diagnosing cancer by administering a composition comprising a humanized LK26 specific antibody. One method of detecting cancer cells involves the steps of administering a labeled antibody (detectable label) to a patient and subsequently detecting where in the body the labeled antibody has bound.

5. DETAILED DESCRIPTION OF THE SPECIFIC EMBODIMENTS

As used herein, the term "humanized" antibody refers to a molecule that has its CDRs (complementarily determining regions) derived from a non-human species immunoglobulin and the remainder of the antibody molecule derived mainly from a human immunoglobulin. The term "antibody" as used herein, unless indicated otherwise, is used broadly to refer to both antibody molecules and a variety of antibody derived molecules. Such antibody derived molecules comprise at least one variable region (either a heavy chain of light chain variable region) and include molecules such as Fab fragments, Fab' fragments, F(ab')$_2$ fragments, Fd fragments, Fabc fragments, Fd fragments, Fabc fragments, Sc antibodies (single chain antibodies), diabodies, individual antibody light chains, individual antibody heavy chains, chimeric fusions between antibody chains and other molecules, and the like.

The term "conventional molecular biology methods" refers to techniques for manipulating polynucleotides that are well known to the person of ordinary skill in the art of molecular biology. Examples of such well known techniques can be found in *Molecular Cloning: A Laboratory Manual 2nd Edition*, Sambrook et al, Cold Spring Harbor, N.Y. (1989). Examples of conventional molecular biology techniques include, but are not limited to, in vitro ligation, restriction endonuclease digestion, PCR, cellular transformation, hybridization, electrophoresis, DNA sequencing, cell culture, and the like.

The term "variable region" as used herein in reference to immunoglobulin molecules has the ordinary meaning given to the term by the person of ordinary skill in the act of immunology. Both antibody heavy chains and antibody light chains may be divided into a "variable region" and a "constant region". The point of division between a variable region and a heavy region may readily be determined by the person of ordinary skill in the art by reference to standard texts describing antibody structure, e.g., Kabat et al "Sequences of Proteins of Immunological Interest: 5th Edition" U.S. Department of Health and Human Services, U.S. Government Printing Office (1991).

The present invention provides humanized antibody molecules specific for LK26 antigen in which at least parts of the CDRs of the heavy and/or light chain variable regions of a human antibody (the receptor antibody) have been substituted by analogous parts of CDRs of a murine monoclonal antibody and the humanized antibody can specifically bind to the same as the LK26 antibody. In a preferred embodiment of the subject invention, the CDR regions of the humanized LK26 specific antibody are derived from the murine antibody LK26. Some of the the humanized antibodies described herein contain some alterations of the acceptor antibody, i.e., human, heavy and/or light chain variable domain framework regions that are necessary for retaining binding specificity of the donor monoclonal antibody. In other words, the framework region of some embodiments the humanized antibodies described herein does not necessarily consist of the precise amino acid sequence of the framework region of a natural occurring human antibody variable region, but contains various substitutions that improve the binding properties of a humanized antibody region that is specific for the same target as the murine LK26 specific antibody. A minimal number of substitutions are made to the framework region in order to avoid large-scale introductions of non-human framework residues and to ensure minimal immunogenicity of the humanized antibody in humans. The donor monoclonal antibody of the present invention is the LK26 murine antibody, which is specific for the human LK26 cancer antigen.

The humanized antibodies of the present invention include complete antibody molecules having full length heavy and light chains, or any fragment thereof, such as the Fab or (Fab')$_2$ fragments, a heavy chain and light chain dimer, or any minimal fragment thereof such as a Fv, an SCA (single chain antibody), and the like, specific for the LK26 antigen molecule.

In addition to providing for humanized LK26 specific antibodies, the subject invention provides for polynucleotides encoding humanized LK26 specific antibodies. The subject polynucleotides may have a wide variety of sequences because of the degeneracy of the genetic code. A person of ordinary skill in the art may readily change a given polynucleotide sequence encoding a humanized LK26 specific antibody into a different polynucleotide encoding the same humanized LK26 specific antibody embodiment. The polynucleotide sequence encoding the antibody may be varied to take into account factors affecting expression such as codon frequency, RNA secondary structure, and the like.

The humanized antibodies of the subject invention may be produced by a variety of methods useful for the production of polypeptides, e.g. in vitro synthesis, recombinant DNA production, and the like. Preferably, the humanized antibodies are produced by recombinant DNA technology.

The humanized LK26 specific antibodies of the invention may be produced using recombinant immunoglobulin expression technology. The recombinant production of immunoglobulin molecules, including humanized antibodies are described in U.S. Pat. No. 4,816,397 (Boss et al), U.S. Pat. No. 4,816,567 (Cabilly et al) U.K. patent GB 2,188,638 (Winter et al), and U.K. patent GB 2,209,757. Techniques for the recombinant expression of immunoglobulins, including humanized immunoglobulins, can also be found, among other places in Goeddel et al, *Gene Expression Technology Methods in Enzymology* Vol. 185 Academic Press (1991), and Borreback, *Antibody Engineering*, W. H. Freeman (1992). Additional information concerning the generation, design, and expression of recombinant antibodies can be found in Mayforth, *Designing Antibodies*, Academic Press, San Diego (1993).

The recombinant humanized anti-LK26 antibodies of the invention may be produced by the following process or other recombinant protein expression methods:

a. Constructing, by conventional molecular biology methods, an expression vector comprising an operon that encodes an antibody heavy chain in which the CDRs and a minimal portion of the variable region framework that are required to retain donor antibody binding specificity are derived from a non-human immunoglobulin, such as the murine LK26 monoclonal antibody, and the remainder of the antibody is derived from a human immunoglobulin, thereby producing a vector for the expression of a humanized antibody heavy chain.

b. Constructing, by conventional molecular biology methods, an expression vector comprising an operon that encodes an antibody light chain in which the CDRs and a minimal portion of the variable region framework that are required to retain donor antibody binding specificity are derived from a non-human immunoglobulin, such as the murine LK26 monoclonal antibody, and the remainder of the antibody is derived from a human immunoglobulin, thereby producing a vector for the expression of humanized antibody light chain.

c. Transferring the expression vectors to a host cell by conventional molecular biology methods to produce a transfected host cell for the expression of humanized anti-LK26 antibodies.

d. Culturing the transfected cell by conventional cell culture techniques so as to produce humanized anti-LK26 antibodies.

Host cells may be cotransfected with two expression vectors of the invention, the first vector containing an operon encoding a heavy chain derived polypeptide and the second containing an operon encoding a light chain derived polypeptide. The two vectors may contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains may comprise cDNA or genomic DNA or both.

The host cell used to express the recombinant antibody of the invention may be either a bacterial cell such as *Escherichia coli*, or preferably a eukaryotic cell. Preferably a mammalian cell such as a chinese hamster ovary cell, may be used. The choice of expression vector is dependent upon the choice of host cell, and may be selected so as to have the desired expression and regulatory characteristics in the selected host cell.

The general methods for construction of the vector of the invention, transfection of cells to produce the host cell of the invention, culture of cells to produce the antibody of the invention are all conventional molecular biology methods. Likewise, once produced, the recombinant antibodies of the invention may be purified by standard procedures of the art, including cross-flow filtration, ammonium sulphate precipitation, affinity column chromatography, gel electrophoresis and the like.

The humanized LK26 specific antibodies of the present invention may be used in conjunction with, or attached to other antibodies (or parts thereof) such as human or humanized monoclonal antibodies. These other antibodies may be reactive with other markers (epitopes) characteristic for the disease against which the antibodies of the invention are directed or may have different specificities chosen, for example, to recruit molecules or cells of the human immune system to the diseased cells. The antibodies of the invention (or parts thereof) may be administered with such antibodies (or parts thereof) as separately administered compositions or as a single composition with the two agents linked by conventional chemical or by molecular biological methods. Additionally the diagnostic and therapeutic value of the antibodies of the invention may be augmented by labelling the humanized antibodies with labels that produce a detectable signal (either in vitro or in vivo) or with a label having a therapeutic property. Some labels, e.g. radionucleotides may produce a detectable signal and have a therapeutic property. Examples of radionuclide labels include $^{125}$I, $^{131}$I, $^{14}$C. Examples of other detectable labels include a fluorescent chromophore such as fluorescein, phycobiliprotein or tetraethyl rhodamine for fluorescence microscopy, an enzyme which produces a fluorescent or colored product for detection by fluorescence, absorbance, visible color or agglutination, which produces an electron dense product for demonstration by electron microscopy; or an electron dense molecule such as ferritin, peroxidase or gold beads for direct or indirect electron microscopic visualization. Labels having therapeutic properties include drugs for the treatment of cancer, such as methotrexate and the like.

The subject invention also provides for a variety of methods for treating and/or detecting cancer cells. These methods involve the administration to of humanized LK26 specific antibodies, either labelled or unlabelled, to a patient. One method of detecting cancer cells in a human involves the step of administering a labeled humanized LK26 specific antibody (labelled with a detectable label) to a human and subsequently detecting bound labeled antibody by the presence of the label.

The recombinant antibodies of this invention may also be used for the selection and/or isolation of human monoclonal antibodies, and the design and synthesis of peptide or non-peptide compounds (mimetics) which would be useful for the same diagnostic and therapeutic applications as the antibodies (e.g. Saragovi et al., (1991) *Science* 253:792–795).

When the humanized LK26 specific antibodies of the invention are used in vitro, the antibodies are typically administered in a composition comprising a pharmaceutical carrier. A pharmaceutical carrier can be any compatible, non-toxic substance suitable for delivery of the monoclonal antibodies to the patient, Sterile water, alcohol, fats, waxes, and inert solids may be included in the carrier. Pharmaceutically accepted adjuvants (buffering agents, dispersing agent) may also be incorporated into the pharmaceutical composition.

The humanized antibodies compositions of the invention may be administered to a patient in a variety of ways. Preferably, the pharmaceutical compositions may be administered parenterally, i.e., subcutaneously, intramuscularly or intravenously. Thus, this invention provides compositions for parenteral administration which comprise a solution of the human monoclonal antibody or a cocktail thereof dissolved in an acceptable carrier, preferably an aqueous carrier. A variety of aqueous carriers can be used, e.g., water, buffered water, 0.4% saline, 0.3% glycine and the like.

These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of antibody in these formulations can vary widely, e.g., from less than about 0.5%, usually at or at least about 1% to as much as 15 or 20% by weight and will be selected primarily based on fluid volumes, viscosities, etc., in accordance with the particular mode of administration selected.

Actual methods for preparing parenterally administrable compositions and adjustments necessary for administration to subjects will be known or apparent to those skilled in the art and are described in more detail in, for example, *Remington's Pharmaceutical Science*, 15th Ed., Mack Publishing Company, Easton, Pa. (1980), which is incorporated herein by reference.

The subject invention provide numerous humanized antibodies specific for the LK26 antigen based on the discovery that the CDR regions of the murine monoclonal antibody could be spliced into a human acceptor framework so as to produce a humanized recombinant antibody specific for the LK26 antigen. Preferred humanized LK26 specific antibodies contain additional change in the framework region (or in other regions) to increasing binding for LK26 antigen. Particularly preferred embodiments of the invention are the exemplified humanized antibody molecules having superior binding properties for LK26.

The following examples are offered by way of illustration of the invention, and should not be interpreted as a limitation of the invention.

5.1. EXAMPLES

In the following examples all necessary restriction and modification enzymes, plasmids and other reagents and materials were obtained from commercial sources unless otherwise indicated.

Unless otherwise indicated, all general recombinant DNA methodology was performed as described in "Molecular Cloning, A Laboratory Manual" (1989) Eds J. Sambrook et al., published by Cold Spring Harbor Laboratory Press, Cold Spring Harbor, N.Y.

In the following examples these abbreviations may be employed:

| | |
|---|---|
| dCTP | deoxycytidine triphosphate |
| dATP | deoxyadenosine triphosphate |
| dGTP | deoxyguanosine triphosphate |
| dTTP | deoxythymidine triphosphate |
| DTT | dithiothreitol |
| C | cytosine |
| A | adenine |

-continued

| | |
|---|---|
| G | guanine |
| T | thymine |
| PBS | phosphate buffered saline |
| PBSB | phosphate buffered saline containing 0.5% (w/v) bovine serum albumin |
| PBST | phosphate buffered saline containing 0.05% (v/v) Tween –20 |

5.1.1. EXAMPLE 1. PRODUCTION OF HUMANIZED ANTIBODIES SPECIFIC FOR THE LK26 ANTIGEN

The source of the donor CDRs used to prepare these recombinant antibodies was a murine monoclonal antibody, mAbLK26, which is specific for the LK26 antigen of certain human cancers. The LK26 monoclonal antibody was produced by immunization of (BALB/c×C57BL/6) $F_1$ mice with LU-75(c) choriocarcinoma cell lines and subsequent production and screening of hybridoma cells. Cytoplasmic RNA was prepared from the mAb LK26 hybridoma cell line by the method of Favoloro, J. et al., (1980), *Methods in Enzymology* 65:718–749). cDNA was synthesized using Ig variable region primers as follows: for the Ig heavy chain variable region (VH), the primer CG2aFOR (5' GGAAGCT-TAGACCGATGGGGCTGTTGTTTTG 3') (SEQ ID NO: 1); for the light chain variable region (VK), the primer CK2FOR (5'GGAAGCTTGAAGATGGATACAGTTGGTGCAGC 3')(SEQ ID NO: 2). cDNA synthesis reactions consisted of 5 μg RNA, 20 pmol CG2aFOR or CK2FOR, 250 μM each of dATP, dCTP, dGTP and dTTP, 100 mM TrisHCl pH8.3, 140 mM KCl, 10 mM DTT, 10 mM MgCl$_2$ and 31.5 units of RNase inhibitor (Pharmacia, Milton Keynes, U.K.) in a total volume of 50 μl. Samples were heated to 70° C. for 10 minutes (min) then slowly cooled to 42° C. over a period of 30 min. 100 units of Moloney Murine Leukaemia virus (M-MLV) reverse transcriptase (Life Technologies Ltd, Paisley, U.K.) was added and incubation at 42° C. continued for 1 hour.

VH and VK cDNAs were then amplified using the polymerase chain reaction (PCR) as described by Saiki, R. K. et al., (1988), *Science* 239:487–491. The primers used were:

CG2aFOR (5' GGAAGCTTAGACCGATGGGGCTGTTGTTTTG 3')
(SEQ ID No: 1)
CK2FOR (5' GGAAGCTTGAAGATGGATACAGTTGGTGCAGC 3')
(SEQ ID NO: 2)
VH1BACK (5' AGGTSMARCTGCAGSAGTCWGG 3')
(SEQ ID NO: 3)
VK4BACK (5' GACATTGAGCTCACCCAGTCTCCA 3')
(SEQ ID NO: 4)

where M=C or A, S=C or G, R=A or G and W=A or T. Such primers and their use in the PCR amplification of mouse Ig DNA are described by Orlandi, R. et al., (1989), *Proc. Natl Acad. Sci. USA*, 86:3833–3837. For PCR amplification of VH, 5 μl RNA/cDNA hybrid was mixed with 25 pmol CG2aFOR and VH1BACK primers. For PCR amplification of VK, 5 μl RNA/cDNA hybrid was mixed with 25 pmol CK2FOR and VK4BACK primers. To these mixtures was added 200 μM each of dATP, dCTP, dGTP and dTTP, 67 mM TrisHCl pH8.8, 17 mM (NH$_4$)$_2$SO$_4$, 10 mM MgCl$_2$, 0.02% (w/v) gelatin and 2.5 units of AmpliTaq DNA polymerase (Perkin Elmer Ltd, Beaconsfield, U.K.) in a total volume of 50 μl. These were then subjected to 25 thermal cycles of PCR at 94° C., 30 s; 50° C., 40 s; 72° C., 30 s; ending with 5 min at 72° C. For cloning and sequencing, amplified DNA was purified by electrophoresis in a low melting point agarose gel and by Elutip-d column chromatography (Schleicher and Schuell, Dussel, Germany). Amplified VH DNA was cut with HindIII and PstI and cloned into M13mp18 or M13mp19 cut with HindIII and PstI (Life Technologies Ltd, Paisley, U.K.). Amplified VK DNA was cut with HindIII and SacI and cloned into HindIII and SacI cut M13mp18 or M13mp19 (Life Technologies Ltd, Paisley, U.K,).

The resulting clones were sequenced by the dideoxy method (Sanger, F. et al., (1977), *Proc. Natl Acad. Sci. USA* 74:5463–5467) using Sequenase (United States Biochemical, Cleveland, Ohio, USA). The DNA and protein sequences of the LK26 VH and VK domains are shown in FIGS. 1 and 2. The location of the CDRs was determined with reference to Kabat, E. A. et al., (1987) "Sequences of Protein of Immunological Interest" US Department of Health and Human Services, US Government Printing Office, and utilizing computer assisted alignment with other VH and VK sequences.

The transfer of the murine CDRs to human frameworks was achieved by oligonucleotide site-directed mutagenesis, based on the method of Nakamye, K. and Eckstein, F. (1986) *Nucleic Acids Res.* 14:9679–9698. The human framework regions chosen to receive the transplanted CDRs were NEWM or KOL and REI for the heavy and light chains respectively. The structures of these proteins have been solved crystallographically. The templates for mutagenesis were human framework region genes containing irrelevant CDRs and consisted of synthetic DNAs cloned into M13 phage (Riechmann, L. et al., (1988) *Nature* 332:323–327).

The oligonucleotides used were:

| | | |
|---|---|---|
| NEWM V(24) | changed to A | (NEWM VHCDR1 oligonucleotide) |
| NEWM S(27) | changed to F | (NEWM VHCDR1 oligonucleotide) |
| NEWM I(48) | changed to V | (NEWM VHCDR2 oligonucleotide) |
| NEWM G(49) | changed to A | (NEWM VHCDR2 oligonucleotide) |
| NEWM V(71) | changed to R | (NEWM VHCDR2 oligonucleotide) |
| KOL S(24) | changed to A | (KOL VHCDR1 oligonucleotide) |
| KOL I(28) | changed to T | (KOL VHCDR1 oligonucleotide) |
| KOL T(68) | changed to A | (KOL VHCDR2 oligonucleotide) |
| KOL S(74) | changed to A | (KOL VHCDR2 oligonucleotide) |

These residues that have been changed are believed to be important for retaining original antigen specificity. Although the invention is not dependent upon any particular explanation for the results obtained by making the additional residue changes, some possible explanations for their significance are as follows:

The change of residues NEWM V(24) and KOL S(24) to the smaller A facilitates the accommodation of the heterologous CDR1 loop. The NEWM S(27) to F change was made because S(27) is an unusual residue in subgroup II human heavy chains (Riechmann et al., (1988) *Nature* 332:323–327). Amino acids VH(27–30, 47–49, 71) are residues of the 'vernier zones' as defined by Foote and Winter (Foote, J. and Winter G. (1992) *J. Mol. Biol.* 224:487–499. These zones are important for adjusting CDR structures to promote antigen binding. This explanation

NEWM VH:

| | |
|---|---|
| VHCDR1 | 5'TGGCTGTCTCACCCAAGACAAGCCATAGCCGCTGAAGGTG AAGCCAGACGCGGTGCAGGTCAGGCT 3' (SEQ ID NO: 5) |
| VHCDR2 | 5'GTTCTTGCTGGTGTCTCTCAGCATTGTCACTCTCCCCTTCAC ACTGTCTGCATAGTAGGTATAACTACCACCACTACTAATCATTG CAACCCACTCAAGACC 3' (SEQ ID NO: 6) |
| VHCDR3 | 5'TGAGGAGACGGTGACCAGGCTCCCTTGGCCCCAGTAAGCAA ACCAGGCGGGATCGTCCCCATGTCTTGCACAATAATA 3' (SEQ ID NO: 7) |

KOL VH:

| | |
|---|---|
| VHCDR1 | 5'CCTGTCTCACCCAAGACAACCCATAGCCGCTGAAGGTGAAGC CAGATGCGGAGCAGGACAGGC 3' (SEQ ID NO: 8) |
| VHCDR2 | 5'GAACAATGTGTTCTTGGCGTTGTCTCGCGATATTGCAAATCT ACCCTTCACACTGTCTGCATAGTAGGTATAACTACCACCACTAC TAATCATTGCAACCCACTCAAGACCTTTTCC 3' (SEQ ID NO: 9) |
| VHCDR3 | 5' CCAATAAGCAAACCAGGCGGGATCGTCCCCATGTCTTGCA CAAAAATAGAC 3' (SEQ ID NO: 10) |

REI VK:

| | |
|---|---|
| VKCDR1 | 5' CTTCTGCTGGTACCAGTGCAAGTTGTTGGAACTT CTGACACTACAGGTGATGGTCAC 3' (SEQ ID NO: 11) |
| VKCDR2 | 5' TCTGCTTGGCACACCAGAAGCCAGGTTGGATGTGCCGTA GATCAGCAGCTT 3' (SEQ ID NO: 12) |
| VKCDR3 | 5' GGTCCCTTGGCCGAACGTGTACATGTACGGGTAACTACT CCACTGTTGGCAGTAGTAGGTGGC 3' (SEQ ID NO: 13) |

A number of additional, murine residues were introduced into the variable region frameworks by extension of the CDR primers. Specifically:

accounts for the changes NEWM S(27) to F, NEWM I(48) to V, NEWM G(49) to A, NEWM V(71) to R and KOL I(28) to T.

For site directed mutagenesis the VH and VK oligonucleotides encoding the murine CDRs were phosphorylated with T4 Kinase (Life Technologies Ltd, Paisley, U.K.). A 25 fold molar excess of each of the three VH or VK primers were added to 0.5 µg of appropriate VH or VK single stranded template DNA in M13 (NEWM VH: M13VHPCR1; KOL VH M13MN14VH; REI: M13VKPCR2) in 40 mM Tris HCl pH7.5, 20 mM MgCl$_2$, 50 mM NaCl and annealed by heating to 90° C. for a few minutes and slowly cooling to 37° C. The annealed DNA was extended with 2.5 units of T7 DNA polymerase (cloned, United States Biochemical, Cleveland, Ohio, USA) in a reaction mixture containing 0.5 units of T4 DNA ligase (Life Technologies Ltd, Paisley, U.K.), 0.25 mM of each of dATP, dGTP, dTTP, and dCTP (Pharmacia, Milton Keynes, U.K.), 40 mM Tris HCl pH7.5, 20 mM MgCl$_2$, 50 mM NaCl, 6.5 mM DTT and 1 mM ATP in a total volume of 30 µl.

The mixture was incubated at room temperature for 1 h. A 1 µl aliquot of this extension/ligation mixture was then used in an asymmetric PCR for the specific amplification of the newly synthesized strand. The reaction contained 1 µl extension/ligation mixture, 250 µM of each of dATP, dGTP, dTTP and dCTP, 67 mM Tris HCl pH8.8, 17 mM (NH$_4$)$_2$SO$_4$, 10 mM MgCl$_2$, 0.02% (w/v) gelatin, 2.5 units of AmpliTaq DNA polymerase and 25 pmol of appropriate oligonucleotide primer (5' AACAGCTATGACCATG 3' (SEQ ID NO:14) for NEWM VH and KOL VH; 5' CTCTCTCAGGGCCAGGCGGTGA 3' (SEQ ID NO:15) for REI VK) in a total volume of 50 µl. The reaction mixtures were subjected to 30 thermal cycles of PCR at 94° C., 30 s; 55° C., 30 s; 72° C., 1 min ending with 72° C., 5 min. The newly synthesized strand was then amplified by adding 20 pmol of appropriate oligonucleotide primer (5' GTAAAACGACGGCCAGT 3' (SEQ ID NO:16) for NEWM VH and KOL VH and 5' GCGGGCCTCTTCGC-TATTACGC 3' (SEQ ID NO:17) for REI VK) and adjusting the reaction mixture to include a further 5 n moles of each of dATP, dGTP, dTTP and dCTP and 2.5 Units of AmpliTaq. The reactions were subjected to a further 20 PCR cycles as above. The amplified VH and VK DNAs were purified from 1.5% w/v low melting point agarose gels by elutip-d column chromatography. Purified DNA was digested with HindIII and BamHI plus RsaI (for VHs) or BstXI (for VKs) (all restriction enzymes were obtained from Life Technologies Ltd, Paisley, U.K.). There is an RsaI site in the parental VHPCR1 and MN14VH and a BstXI site in the parental VKPCR2 but these sites are deleted during mutagenesis. These digestions therefore select for newly synthesized DNA. The HindIII/BamHI digested VH and VK DNAs were ligated into HindIII/BamHI cut M13mp18 or M13mp19 (both from Pharmacia, Milton Keynes, U.K.) and transformed into competent *E. coli* TG1 (Amersham International plc, Amersham, U.K.). Single stranded DNA was prepared from individual 'plaques' and sequenced by the dideoxy method using Sequenase (United States Biochemical, Cleveland, Ohio, USA) according to Manufacturer's instructions. Triple CDR mutants were identified in this way and selected for construction of VH and VK expression vectors.

Figure 4:
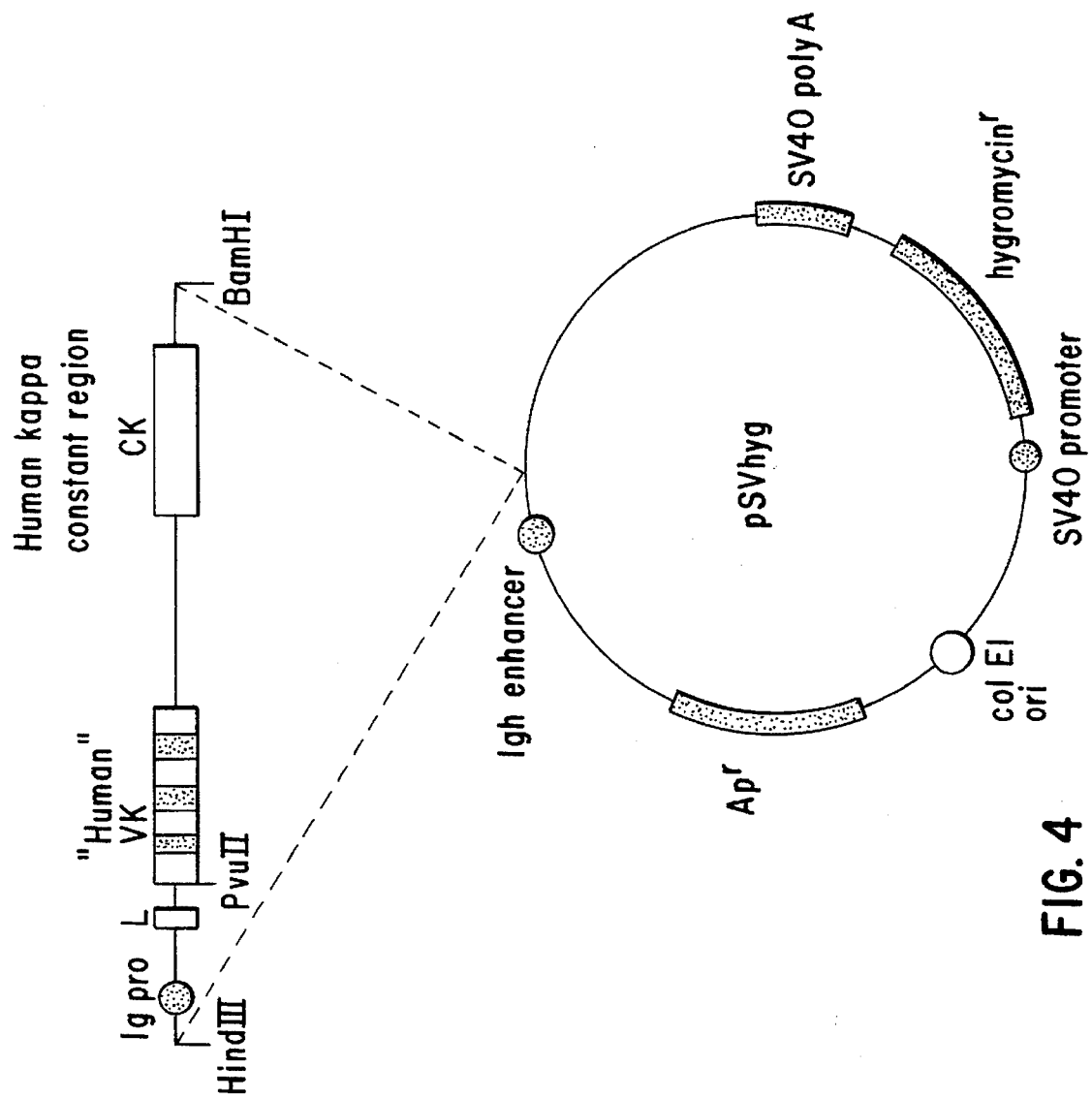
FIG. 4 shows the vector pSVhyg for the expression of chimeric or humanized light chains in mammalian cells.
Figure 5:
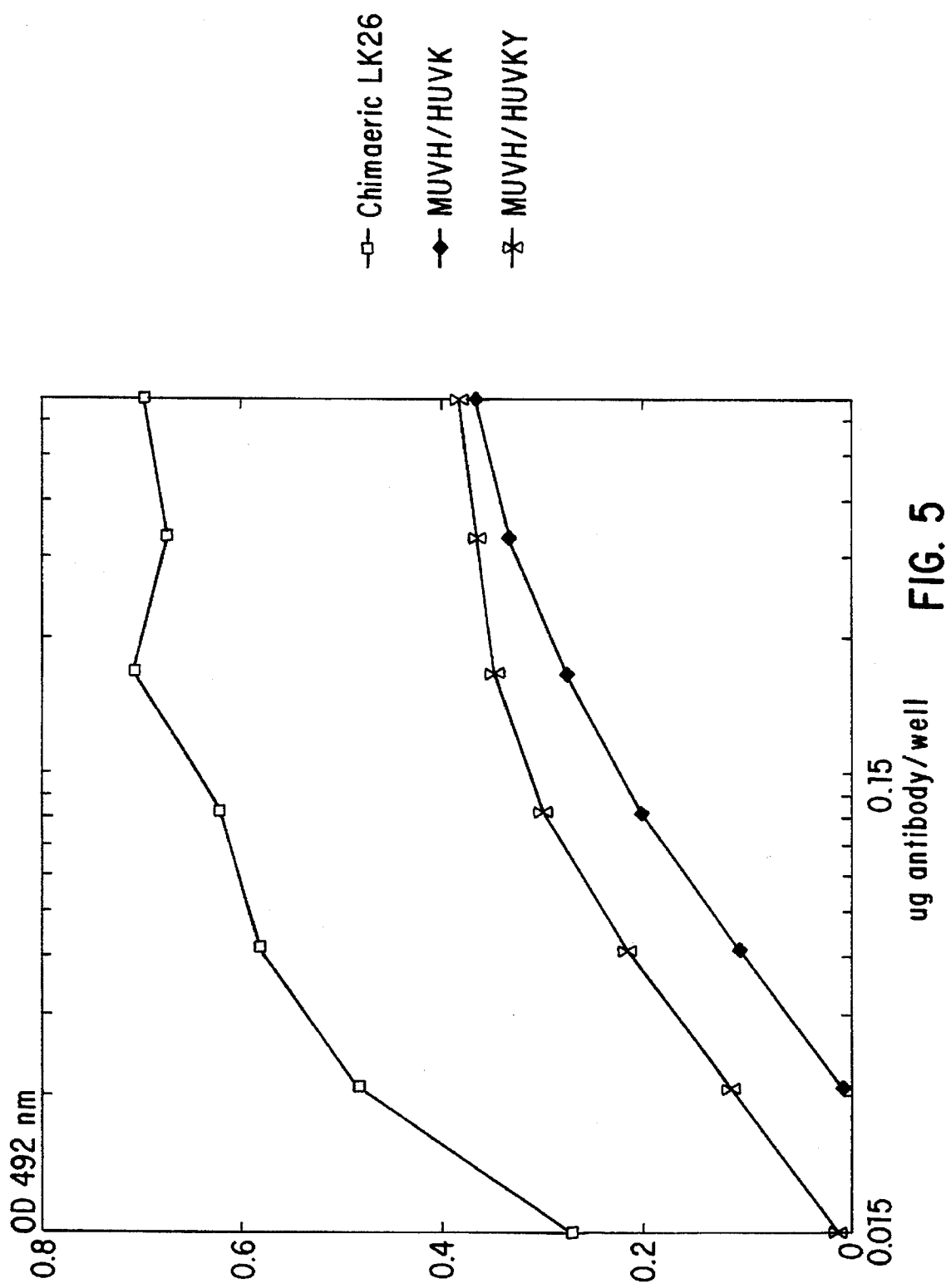
Figure 6:
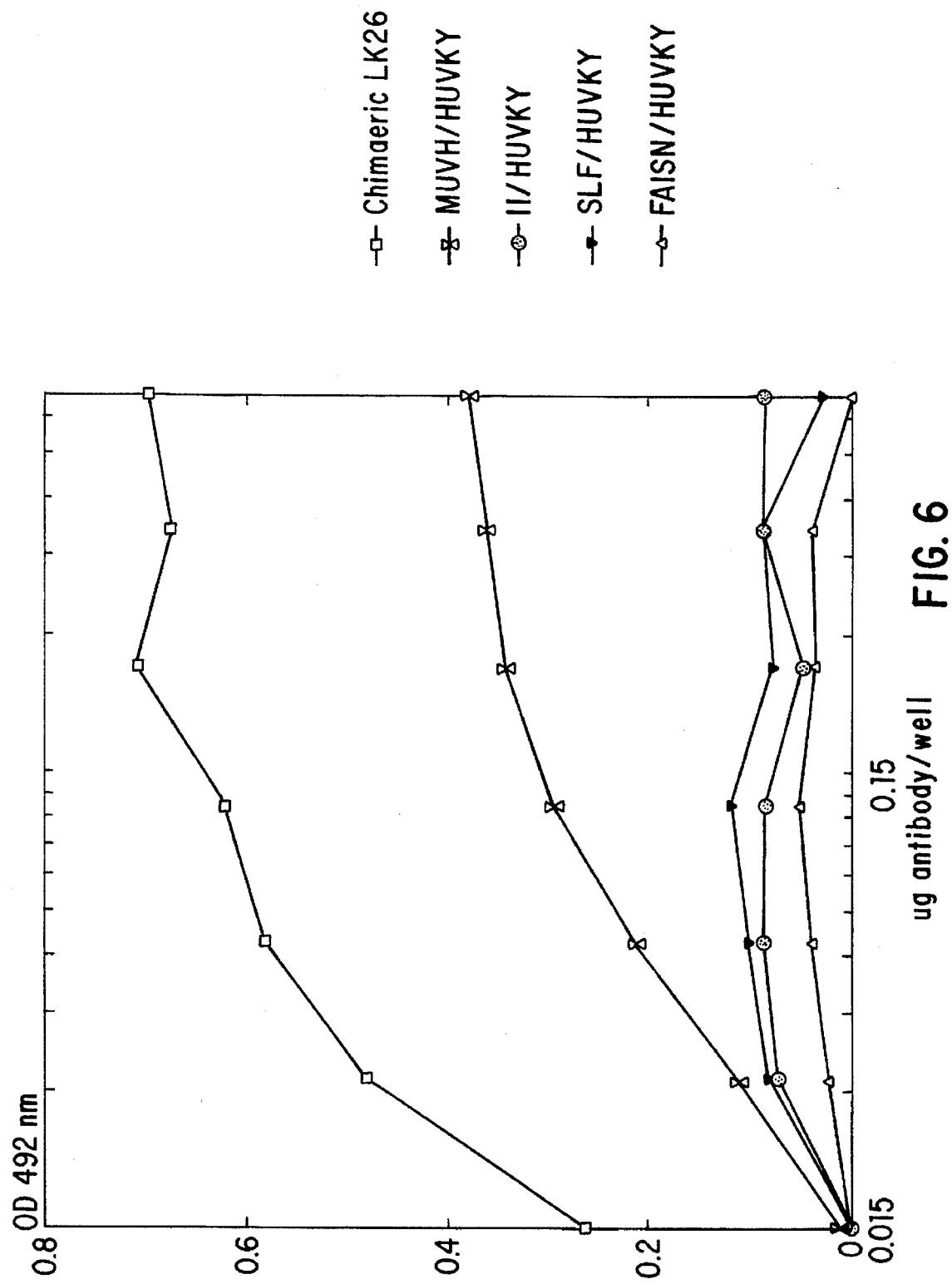
Figure 7:
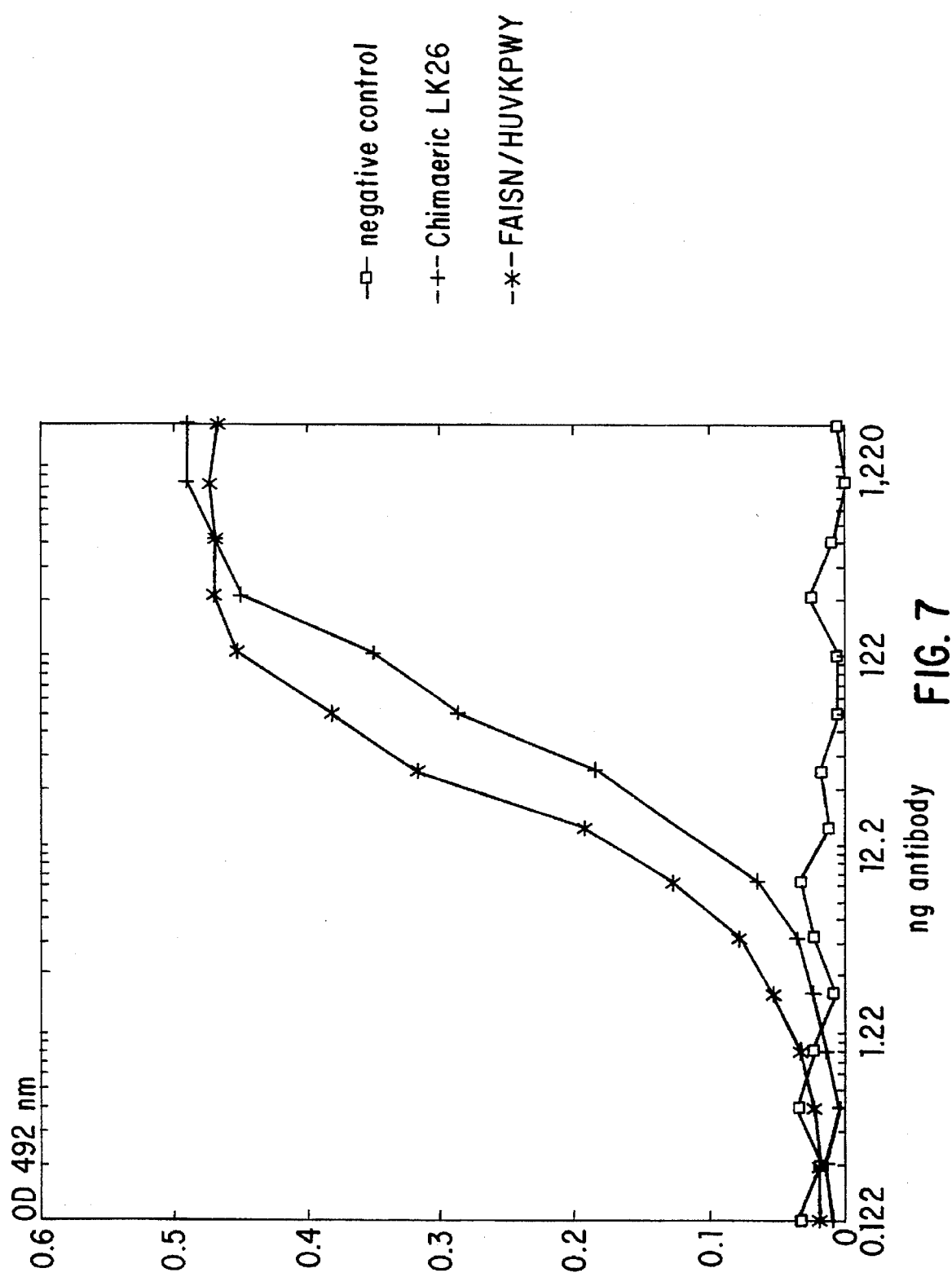
Figure 8:
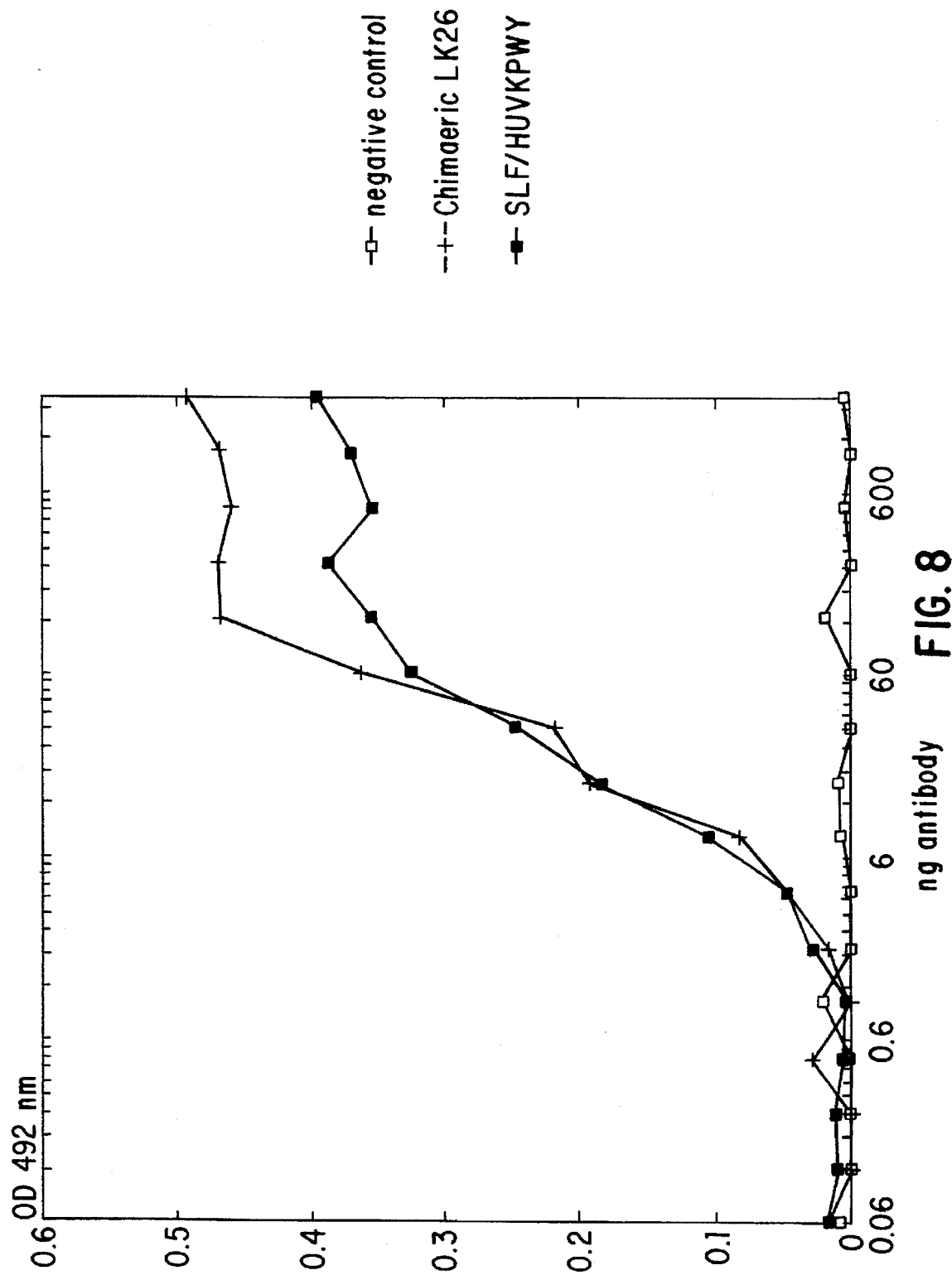
Figure 9:
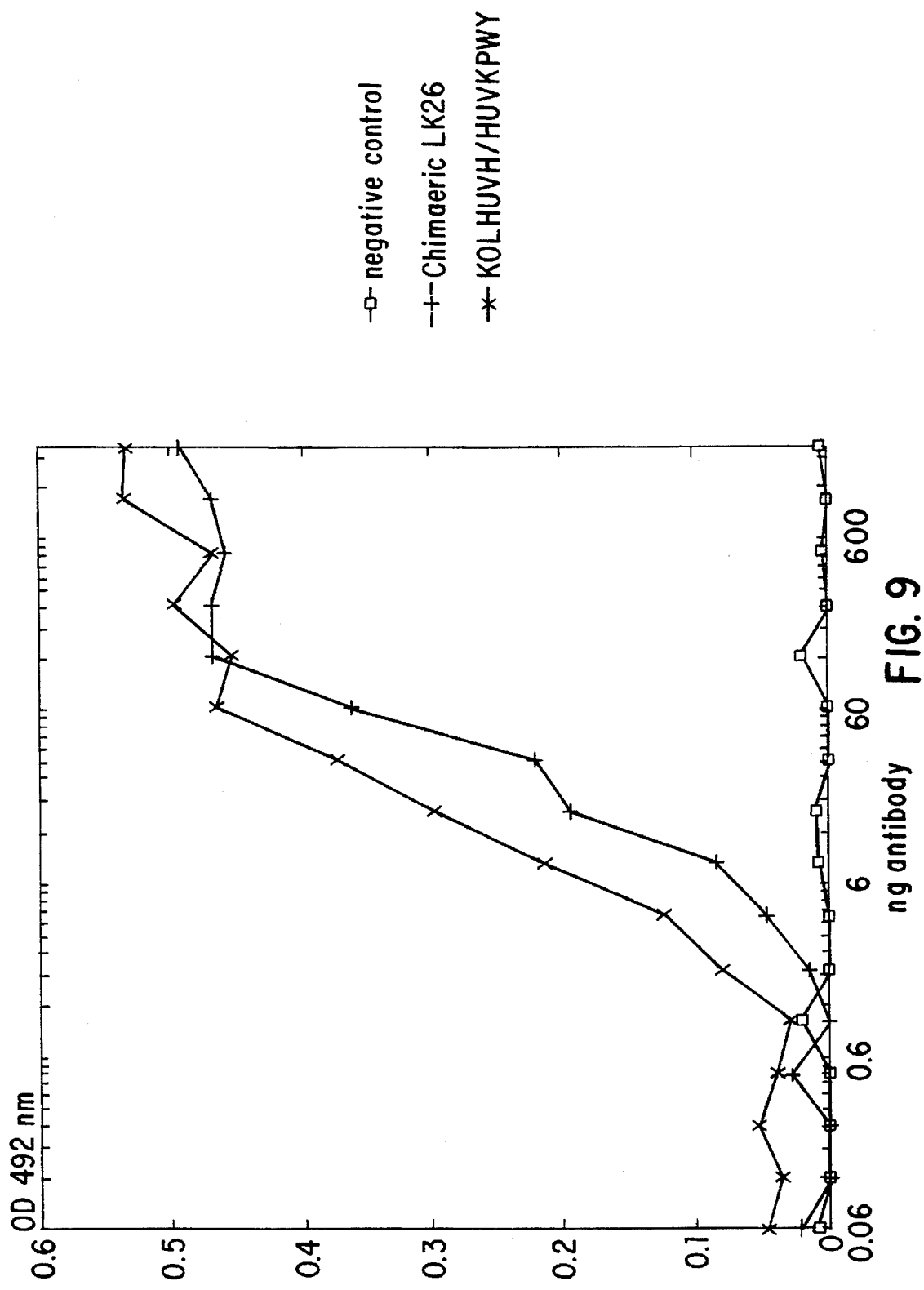
Figure 10:
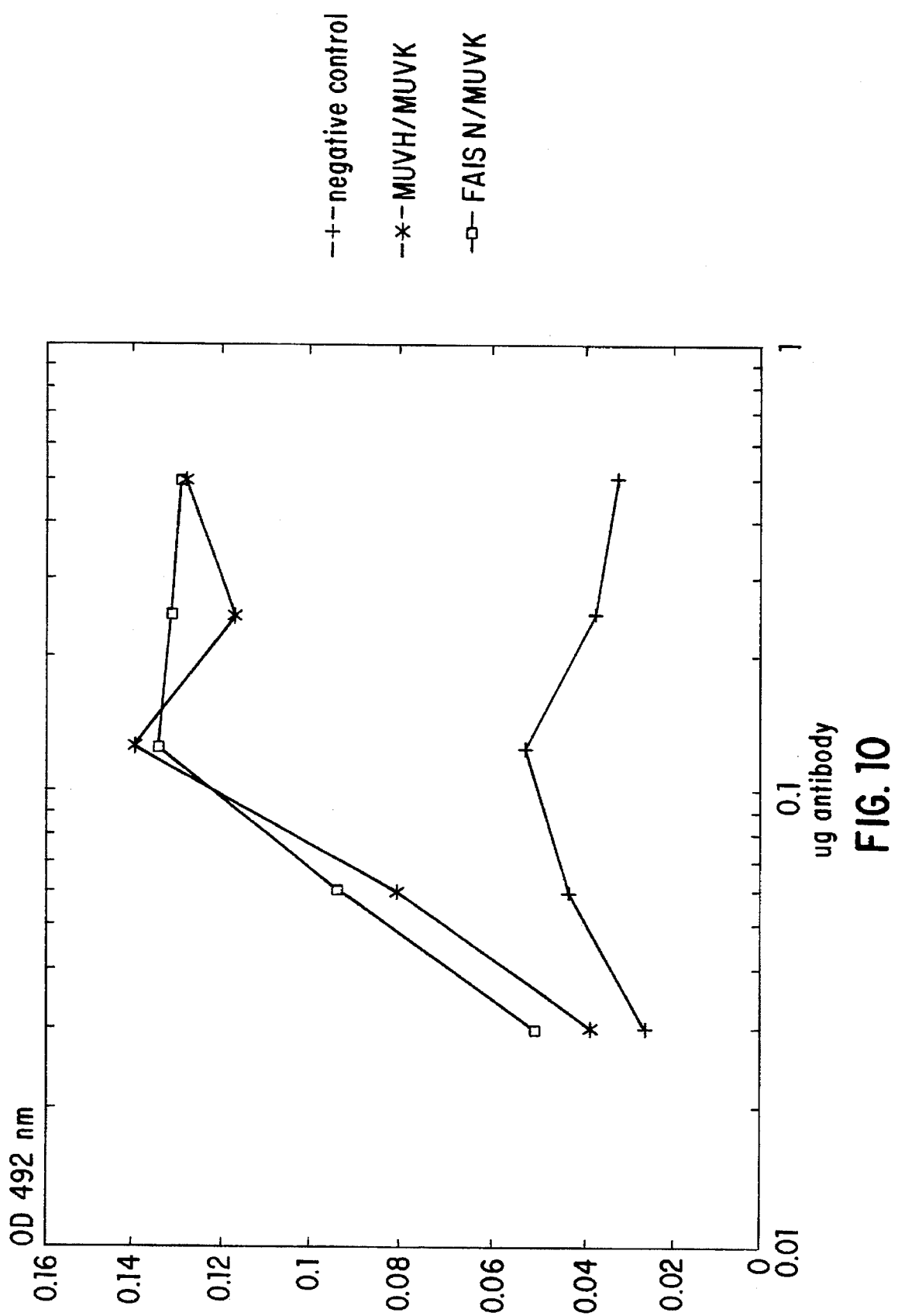
Figure 11:
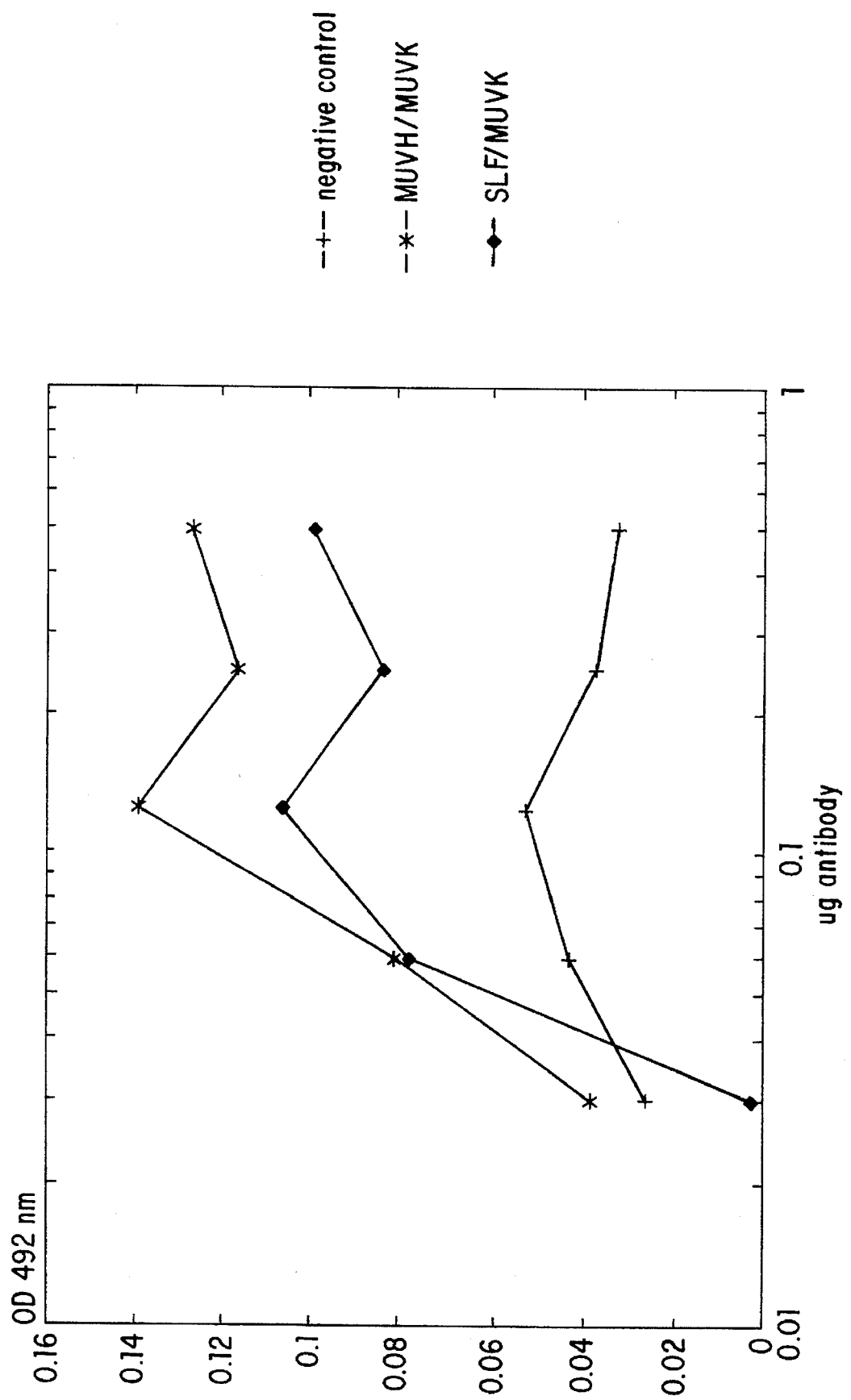
Figure 12:
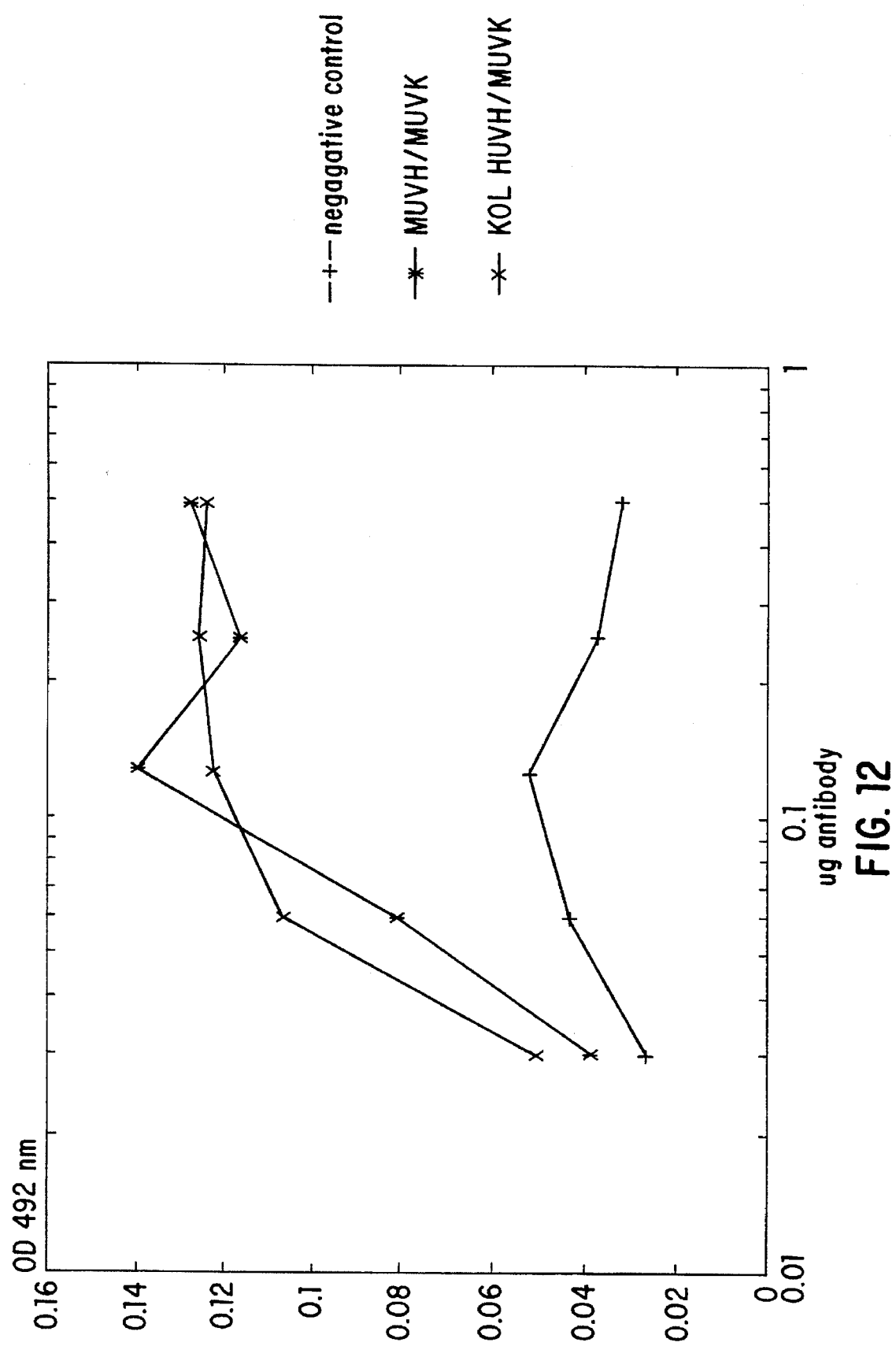

The expression vectors for the humanized VH and VK genes, pSVgpt and pSVhyg are shown in FIGS. 3 and 4. The humanized VH genes, together with the immunoglobulin heavy chain promoter, appropriate splice sites and signal peptide sequences were excised from the M13 clones with HindIII and BamHI and ligated into the heavy chain expression vector, pSVgpt. This vector contains the murine heavy chain immunoglobulin enhancer, the gpt gene under control of the SV40 promoter/enhancer for selection in mammalian cells, the human IgG1 constant region domain and sequences for replication and selection in *E. coli*. The humanized VK gene was cloned into the light chain expression vector pSVhyg in the same way. All features of pSVhyg are the same as in pSVgpt except that the gpt gene is replaced by the gene for hygromycin resistance (hyg) and a human kappa constant region is included instead of the IgG1 constant region.

For transfection into mammalian cells 10 µg of the heavy chain expression vector DNA and 20 µg of the light chain vector DNA were linearized by digestion with PvuI (Life Technologies Ltd, Paisley, U.K.), coprecipitated with ethanol and redissolved in 20 µl of water. The recipient cell line was NSO, a non-immunoglobulin producing mouse myeloma, obtained from the European collection of Animal Cell Cultures, Porton, U.K., ECAC No. 85110505 cells were grown in Dulbecco's Modified Eagle's Medium supplemented with 10% foetal calf serum and antibiotics (DMEM) (Life Technologies Ltd, Paisley, U.K.). Approximately 10$^7$ NSO cells were harvested by centrifugation and resuspended in 0.5 ml DMEM, the digested DNA was added and the cells transferred to a cuvette and placed on ice for 5 min. A single pulse of 170 volts, 960µ farads was administered (Genepulser, BioRad, Richmond, Calif., U.S.A.). After a further 30 min on ice the cells were replaced in a flask in 20 ml DMEM and allowed to recover for 24 hours. After this time the cells were distributed into a 24 well plate in selective medium (DMEM with 0.8 µg/ml mycophenolic acid and 250 µg/ml xanthine). After 3 to 4 days the medium was changed for fresh selective medium. Colonies of transfected cells were visible after 10 to 14 days.

The production of human antibody in the wells containing transfected clones was measured by ELISA. Capture antibody, goat anti-human IgG, gamma chain specific (Sera-Lab Ltd, Crawley Down, U.K.) was diluted to 5 µg/ml in 50 mM carbonate buffer pH9.6, and used to coat polystyrene ELISA plates (Dynatech Immulon 1), 200 µl per well, overnight at 4° C. After washing 3 times with PBST, 50–100 µl of the culture medium to be screened was added to the wells and incubated at 37° C. for 60 min. The wells were washed again with PBST and the reporter antibody, peroxidase-conjugated goat anti-human IgG, gamma chain specific (Sera-Lab Ltd, Crawley Down, U.K.) or peroxidase-conjugated goat anti-human kappa chain (Sera-Lab Ltd, Crawley Down, U.K) was added at 100 ng per well and the plate incubated for a further 60 min. The plate was washed as before then the colour was developed. Substrate buffer was prepared by mixing 100 mM citric acid and 100 mM disodium hydrogen phosphate to pH5.0. 25 mg of o-phenylenediamine was dissolved in 50 ml and 5 µl of 30% hydrogen peroxide added just before use. 200 µl was dispensed per well and incubated at room temperature in the dark. The reaction was stopped by addition of 50 µl per well of 12.5% sulphuric acid and the absorbances were read at 492 nm.

Positive cell clones were expanded for antibody purification. For the final expansion to production volume the cells were diluted in DMEM containing 10% IgG-free fetal calf serum. For small scale purification 500 ml of conditioned medium from static flask or spinner cultures was harvested by centrifugation. 0.1 volumes of 1.0M TrisHCl pH8.0 and 0.5 to 1.0 ml of Protein A-agarose (Boehringer Mannheim, Lewes, U.K.) were added. This was stirred overnight at room temperature then collected on a disposable column. This was washed with 10 column volumes of 0.1M TrisHCl pH8.0, 10 column volumes of 0.01M TrisHCl pH8.0 and eluted with 0.1M glycine buffer, pH3.0. 1.0 ml fractions were collected into tubes containing 100 µl of 1.0M TrisHCl, pH8.0. Fractions containing antibody were pooled and dialysed against PBS. The concentrations of the antibody preparations were determined using a Micro BCA Protein Assay Reagent Kit (Pierce, Rockford, USA). Samples were checked by running on 10% SDS-polyacrylamide gels.

The chimeric LK26 antibody, in which the murine constant region domains of the heavy and light chains had been replaced by the human constant regions used in the humanized antibody, was constructed as described by Orlandi et al., (1989). Three hybrid chimeric/humanized antibodies were constructed consisting of the chimeric heavy chain with the humanized light chain and the humanized heavy chain (from NEWM and KOL mutagenesis) with the chimeric light chain.

None of these hybrid antibodies showed binding to the SW620 target cells equivalent to the chimeric antibody. This indicates that further framework changes, in both the VH and VK chains, are necessary to restore antigen binding.

Four further versions of the LK26HuVH and two further versions of the LK26HuVK were designed. The amino acid sequences of these VHs and VKs are shown in Table 1.

Table 1 shows the variable region sequences of LK26HuVH, LK26HuVHFAIS,N, LK26HuVH SLF, LK26HuVHI,I, LK26KOLHuVH, LK26HuVK, LK26HuVKY and LK26HuVKPW,Y. Murine framework residues are shown in lower case. Some framework residues in NEWM and REI are unusual for human subgroup II heavy chains or human subgroup I kappa chains, respectively, these have been replaced by the residues commonly found at these positions and are underlined in the table.

The additional changes to the HuVH and HuVK constructs are shown below (numbering according to Kabat et al., ibid):

LK26HuVHFAIS,N (67–70, 73)
LK26HuVHSLF (77–79)
LK26HuVHI,I (89,91)
LK26HuVKY (71)
LK26HuVKPW,Y (46–47, 71)

These new versions were constructed by mutagenesis of the original reshaped heavy and light chain M13 single stranded DNA clones. The method of Higuchi, R. et al. (1988) *Nucleic Acids Res.* 16:7351–7367, which utilizes overlapping PCR amplification with mutagenic primers, was employed. The modified variable regions were cloned into the expression vector pSVgpt or pSVhyg as before and cotransfected with either the MuVK or MuVH plasmids into NSO cells. Antibody producing cell clones were selected, expanded and purified for testing. Subsequent to this, fully humanized version antibodies consisting of the modified HuVHs and HuVKs were prepared in the same way.

Another version of the humanized light chain produced was LK26HuVKPW. LK26HuVKPW is similar to LK26HuVKPW,Y, but lacks the change at position 71.

5.1.2. EXAMPLE 2. SPECIFIC BINDING OF HUMANIZED LK26 ANTIBODIES TO CARCINOMA CELLS

The recombinant antibodies have been tested in ELISAs using the SW620 target cells. The ELISA method used is as follows:

SW620 cells are diluted to $1.5 \times 10^5 - 2.5 \times 10^5$ cells/ml in DMEM, 10% FCS and 200 µl (ie $3-5 \times 10^4$ cells) added to each well. Cells are grown until nearly confluent (about 2 days). Plates are washed 2× with PBS and 100 µl antibody (diluted in DMEM) added. Incubation is carried out at 4° C. for 1 hour. The wells are washed 3× with PBS and 100 µl of appropriate reporter antibody added, ie either goat anti-human IgG1, HRPO conjugate (Sera-lab, 0.4 mg/ml, diluted 1:500 in DMEM) or goat anti-mouse IgG1, HRPO conjugate (Sera-lab, 0.4 mg/ml, diluted 1:500 in DMEM), incubation is carried out at 4° C. for 1 hour. Wells are washed 3× with PBS and bound reporter antibody detected using $H_2O_2$ and o-phenylenediaminedihydrochloride and the OD 492 nm measured.

The humanized antibodies tested in ELISAs are LK26HuVHSLF/HuVKPW,Y, LK26HuVHFAIS,N/HuVKPW,Y and LK26KOLHUVH/HuVKPW,Y. The data are presented graphically below. The test data of the various recombinant antibodies indicate that of particular value for the restoration of antigen binding is the inclusion of the P and W residues into the humanized light chain. Furthermore, the data show that these inclusions facilitate the proper association of the VH and VL domains. This invention therefore also relates to the inclusion into the humanized antibody of these and other VH and VL residues to facilitate proper VH and VL association and thereby antigen binding.

The test data indicates that these humanized antibodies retain the binding properties of the original murine and chimeric antibodies. In particular the LK26HuVHFAIS,N/HuVKPW,Y and the LK26KOLHuVH/HuVKPW,Y exhibit binding affinities higher than the chimeric antibody. Such recombinant antibodies (of which these are examples) therefore provide for novel, recombinant antibody molecules for the diagnosis and therapy of human cancers characterized by the expression of the LK26 antigen.

TABLE 1

| | |
|---|---|
| LK26HuVH: | QVQLQESGPGLVRPSQTLSLTCTaSGfIFSGYGLSWVRQ PPGRGLEWvaMISSGGSYTYYADSVKGRVTMLrDTSKNQ FSLRLSSVTAADTAVYYCARHGDDPAWFAYWGQGSLVTV SS (SEQ ID NO: 18) |
| LK26HuVHFAIS, N: | QVQLQESGPGLVRPSQTLSLTCTaSGfIFSGYGL SWVRQPPGRGLEWvaMISSGGSYTYYADSVKGRf aisrDnSKNQFSLRLSSVTAADTAVYYCARHGDD PAWFAYWGQGSLVTVSS (SEQ ID NO: 19) |
| LK26HuVHI, I: | QVQLQESGPGLVRPSQTLSLTCTaSGfIFSGYGLSWVRQ PPGRGLEWvaMISSGGSYTYYADSVKGRVTMLrDTSKNQ FSLRLSSVTAADTAiYiCARHGDDPAWFAYWGQGSLVTV SS (SEQ ID NO: 20) |
| LK26HuVHSLF: | QVQLQESGPGLVRPSQTLSLTCTaSGfIFSGYGLSWVRQ PPGRGLEWvaMISSGGSYTYYADSVKGRVTMLrDTSKNs lfLRLSSVTAADTAVYYCARHGDDPAWFAYWGQG<u>TT</u>VTV |

TABLE 1-continued

| | |
|---|---|
| | SS<br>(SEQ ID NO: 21) |
| LK26KOLHuVH: | EVQLVESGGGVVQPGRSLRLSCSaSGFtFSGYGLSWVRQ<br>APGKGLEWVAMISSGGSYTYYADSVKGRFaISRDNaKNT<br>LFLQMDSLRPEDTGVYFCARHGDDPAWFAYWGQGTPVTV<br>SS<br>(SEQ ID NO: 22) |
| LK26HuVK: | DIQLTQSPSSLSASVGDRVTITCSVSSSISSNHLHWYQQ<br>KPGKAPKLLIYGTSNLASGVPSRFSGSGSGTDFTFTISS<br>LQPEDIATYYCQQWSSYPYMYTFGQGTKVEIK+ee<br>(SEQ ID NO: 23) |
| LK26HuVKY: | DIQ+e,uns LTQSPSSLSASVGDRVTITCSVSSSISSNNLHWYQQ<br>KPGKAPKLLIYGTSNLASGVPSRFSSGSGTDYTFTISS<br>LQPEDIATYYCQQWSSYPYMYTFGQGTKVEIK<br>(SEQ ID NO: 24) |
| LK26HuVKPW, Y: | DIQLTQSPSSLSASVGDRVTITCSVSSSISSNNLHWYQQ<br>KPGKAPKpwIYGTSNLASGVPSRFSGSGSGTDFTFTISS<br>LQPEDIATYYCQQWSSYPYMYTFGQGTKVEIK<br>(SEQ ID NO: 25) |

Incorporation by Reference

All patents, patents applications, and publications cited are incorporated herein by reference.

Equivalents

The foregoing written specification is considered to be sufficient to enable one skilled in the art to practice the invention. Indeed, various modifications of the above-described makes for carrying out the invention which are obvious to those skilled in the field of molecular biology or related fields are intended to be within the scope of the following claims.

---

What is claimed is:

1. A polypeptide having a sequence selected from the group consisting of LK26HuVK; LK26HuVKY; LK26HuVKPW; LK26HuVKPW,Y; LK26HuVH; LK26HuVH FAIS,N; LK26HuVH SLF; LK26HuVH I,I; and LK26KOLHuVH.

2. An antibody having a humanized variable region wherein the variable region light chain is selected from the group consisting of LK26HuVK; LK26HuVKY; LK26HuVKPW; and LK26HuVKPW,Y, and the variable region heavy chain is selected from the group consisting of LK26HuVH; LK26HuVH FAIS,N; LK26HuVH SLF; LK26HuVH I, I; and LK26KOLHuVH.

* * * * *

UNITED STATES PATENT AND TRADEMARK OFFICE
CERTIFICATE OF CORRECTION

PATENT NO. : 5,646,253  
DATED : June 8, 1997  
INVENTOR(S) : Wallace et al.

Page 1 of 1

It is certified that error appears in the above-identified patent and that said Letters Patent is hereby corrected as shown below:

Column 9,  
Lines 54-55, change "CTTCTGCTGGTACCAGTGCAAGTTGTTAACTTCTGACACTACAGGTGATGGTCAC" to -- CTTCTGCTGGTACCAGTGCAAGTTGTTGGAACTTATACTTGAGCTGACTACAGGTGATGGTCAC --.

Column 14,  
Line 3, after "LKHuVKPW,Y" add -- (SEQ ID NO: 25, with the proviso that amino acid 72 is Tyr rather than Phe) --.  
Line 29, change "LKHuVKPW,Y" to -- LKHuVKPW,Y (SEQ ID NO: 25, with the proviso that amino acid 72 is Tyr, rather than Phe) --.  
Line 43, (both occurrences) change "HuVKPW,Y" to -- LK26HuVKPW,Y (SEQ ID. NO: 25, with the proviso that amino acid 72 is Tyr, rather than Phe) --.

Column 15,  
Line 13, change "PSRFSSGS ..." to -- PSRFSSGSGS. --.

Column 33,  
Line 10, change "LK26HuVKPW,Y" to -- LK26HuVKPW,Y (SEQ ID NO: 25, with the proviso that amino acid 72 is Tyr, rather than Phi) --.

Column 34,  
Line 9, change "LK26HuVKPW,Y" to -- LK26HuVKPW,Y (SEQ ID NO: 25, with the proviso that amino acid 72 is Tyr, rather than Phi) --.

Signed and Sealed this

Twenty-ninth Day of November, 2005

JON W. DUDAS  
*Director of the United States Patent and Trademark Office*

UNITED STATES PATENT AND TRADEMARK OFFICE
CERTIFICATE OF CORRECTION

| | |
|---|---|
| PATENT NO. | : 5,646,253 |
| APPLICATION NO. | : 08/207996 |
| DATED | : July 8, 1997 |
| INVENTOR(S) | : Thomas P. Wallace et al. |

It is certified that error appears in the above-identified patent and that said Letters Patent is hereby corrected as shown below:

Column 13, line 32:

Change "LK26HuVHFAIS,N(67-70, 73)" to -- LK26HuVHFAIS,N (68-71, 74) --.

Column 13, line 33:

Change "LK26HuVHSLF (77-79)" to -- LK26HuVHSLF (78-80) --.

Column 13, line 34:

Change "LK26HuVHI,I (89, 91)" to -- LK26HuVHI,I (93, 95) --.

Column 13, line 35:

Change "LK26HuVKY (71) to -- LK26HuVKY (72) --.

Column 13, line 36:

Change "LK26HuVKPW,Y (46-47, 71)" to -- LK26HuVKPW,Y (47-48, 72) --.

Signed and Sealed this

Fifteenth Day of January, 2008

JON W. DUDAS
*Director of the United States Patent and Trademark Office*

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GGAAGCTTAG ACCGATGGGG CTGTTGTTTT G        31

( 2 ) INFORMATION FOR SEQ ID NO:2:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GGAAGCTTGA AGATGGATAC AGTTGGTGCA GC        32

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

AGGTSMARCT GCAGSAGTCW GG　　　　　　　　　　　22

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GACATTGAGC TCACCCAGTC TCCA　　　　　　　　　　24

( 2 ) INFORMATION FOR SEQ ID NO:5:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

TGGCTGTCTC ACCCAAGACA AGCCATAGCC GCTGAAGGTG AAGCCAGACG　　50

CGGTGCAGGT CAGGCT　　　　　　　　　　　　　　　　　　　　　66

( 2 ) INFORMATION FOR SEQ ID NO:6:

( i ) SEQUENCE CHARACTERISTICS:
        ( A ) LENGTH: 102 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GTTCTTGCTG GTGTCTCTCA GCATTGTCAC TCTCCCCTTC ACACTGTCTG　　50

CATAGTAGGT ATAACTACCA CCACTACTAA TCATTGCAAC CCACTCAAGA　　100

CC　　　　　　　　　　　　　　　　　　　　　　　　　　　　　　102

( 2 ) INFORMATION FOR SEQ ID NO:7:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

TGAGGAGACG GTGACCAGGC TCCCTTGGCC CCAGTAAGCA AACCAGGCGG　　50

GATCGTCCCC ATGTCTTGCA CAATAATA　　　　　　　　　　　　　　78

( 2 ) INFORMATION FOR SEQ ID NO:8:

( i ) SEQUENCE CHARACTERISTICS:
        ( A ) LENGTH: 63 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:8:

```
CCTGTCTCAC CCAAGACAAC CCATAGCCGC TGAAGGTGAA GCCAGATGCG        50

GAGCAGGACA GGC                                                63
```

(2) INFORMATION FOR SEQ ID NO:9:

(i) SEQUENCE CHARACTERISTICS:
(A) LENGTH: 117 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

```
GAACAATGTG TTCTTGGCGT TGTCTCGCGA TATTGCAAAT CTACCCTTCA        50

CACTGTCTGC ATAGTAGGTA TAACTACCAC CACTACTAAT CATTGCAACC        100

CACTCAAGAC CTTTTCC                                            117
```

(2) INFORMATION FOR SEQ ID NO:10:

(i) SEQUENCE CHARACTERISTICS:
(A) LENGTH: 51 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:10:

```
CCAATAAGCA AACCAGGCGG GATCGTCCCC ATGTCTTGCA CAAAAATAGA        50

C                                                             51
```

(2) INFORMATION FOR SEQ ID NO:11:

(i) SEQUENCE CHARACTERISTICS:
(A) LENGTH: 66 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:11:

```
CTTCTGCTGG TACCAGTGCA AGTTGTTGGA ACTTATACTT GAGCTGACAC        50

TACAGGTGAT GGTCAC                                             66
```

(2) INFORMATION FOR SEQ ID NO:12:

(i) SEQUENCE CHARACTERISTICS:
(A) LENGTH: 51 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

```
TCTGCTTGGC ACACCAGAAG CCAGGTTGGA TGTGCCGTAG ATCAGCAGCT        50

T                                                             51
```

( 2 ) INFORMATION FOR SEQ ID NO:13:

( i ) SEQUENCE CHARACTERISTICS:
           ( A ) LENGTH: 63 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:13:

```
GGTCCCTTGG CCGAACGTGT ACATGTACGG GTAACTACTC CACTGTTGGC        50

AGTAGTAGGT GGC                                                63
```

( 2 ) INFORMATION FOR SEQ ID NO:14:

( i ) SEQUENCE CHARACTERISTICS:
           ( A ) LENGTH: 16 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:14:

```
AACAGCTATG ACCATG                                             16
```

( 2 ) INFORMATION FOR SEQ ID NO:15:

( i ) SEQUENCE CHARACTERISTICS:
           ( A ) LENGTH: 22 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:15:

```
CTCTCTCAGG GCCAGGCGGT GA                                      22
```

( 2 ) INFORMATION FOR SEQ ID NO:16:

( i ) SEQUENCE CHARACTERISTICS:
           ( A ) LENGTH: 17 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:16:

```
GTAAAACGAC GGCCAGT                                            17
```

( 2 ) INFORMATION FOR SEQ ID NO:17:

( i ) SEQUENCE CHARACTERISTICS:
           ( A ) LENGTH: 22 base pairs
           ( B ) TYPE: nucleic acid
           ( C ) STRANDEDNESS: single
           ( D ) TOPOLOGY: linear ( i i ) MOLECULE TYPE: DNA (genomic)

( x i ) SEQUENCE DESCRIPTION: SEQ ID NO:17:

```
GCGGGCCTCT TCGCTATTAC GC                                      22
```

( 2 ) INFORMATION FOR SEQ ID NO:18:

( i ) SEQUENCE CHARACTERISTICS:
    ( A ) LENGTH: 119 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:18:

```
Gln Val Gln Leu Gln Glu Ser Gly Pro Gly Leu Val Arg Pro Ser Gln
 1               5                  10                  15
Thr Leu Ser Leu Thr Cys Thr Ala Ser Gly Phe Thr Phe Ser Gly Tyr
            20                  25                  30
Gly Leu Ser Trp Val Arg Gln Pro Pro Gly Arg Gly Leu Glu Trp Val
            35                  40                  45
Ala Met Ile Ser Ser Gly Gly Ser Tyr Thr Tyr Tyr Ala Asp Ser Val
        50                  55                  60
Lys Gly Arg Val Thr Met Leu Arg Asp Thr Ser Lys Asn Gln Phe Ser
65                      70                  75                  80
Leu Arg Leu Ser Ser Val Thr Ala Ala Asp Thr Ala Val Tyr Tyr Cys
                85                  90                  95
Ala Arg His Gly Asp Asp Pro Ala Trp Phe Ala Tyr Trp Gly Gln Gly
                100                 105                 110
Ser Leu Val Thr Val Ser Ser
            115
```

( 2 ) INFORMATION FOR SEQ ID NO:19:

( i ) SEQUENCE CHARACTERISTICS:
    ( A ) LENGTH: 119 amino acids
    ( B ) TYPE: amino acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:19:

```
Gln Val Gln Leu Gln Glu Ser Gly Pro Gly Leu Val Arg Pro Ser Gln
 1               5                  10                  15
Thr Leu Ser Leu Thr Cys Thr Ala Ser Gly Phe Thr Phe Ser Gly Tyr
            20                  25                  30
Gly Leu Ser Trp Val Arg Gln Pro Pro Gly Arg Gly Leu Glu Trp Val
            35                  40                  45
Ala Met Ile Ser Ser Gly Gly Ser Tyr Thr Tyr Tyr Ala Asp Ser Val
        50                  55                  60
Lys Gly Arg Phe Ala Ile Ser Arg Asp Asn Ser Lys Asn Gln Phe Ser
65                      70                  75                  80
Leu Arg Leu Ser Ser Val Thr Ala Ala Asp Thr Ala Val Tyr Tyr Cys
                85                  90                  95
Ala Arg His Gly Asp Asp Pro Ala Trp Phe Ala Tyr Trp Gly Gln Gly
                100                 105                 110
Ser Leu Val Thr Val Ser Ser
            115
```

( 2 ) INFORMATION FOR SEQ ID NO:20:

( i ) SEQUENCE CHARACTERISTICS:
    ( A ) LENGTH: 119 amino acids
    ( B ) TYPE: amino acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:20:

| Gln | Val | Gln | Leu | Gln | Glu | Ser | Gly | Pro | Gly | Leu | Val | Arg | Pro | Ser | Gln |
|---|---|---|---|---|---|---|---|---|---|---|---|---|---|---|---|
| 1 | | | | 5 | | | | | 10 | | | | | 15 | |
| Thr | Leu | Ser | Leu | Thr | Cys | Thr | Ala | Ser | Gly | Phe | Thr | Phe | Ser | Gly | Tyr |
| | | | 20 | | | | | 25 | | | | | 30 | | |
| Gly | Leu | Ser | Trp | Val | Arg | Gln | Pro | Pro | Gly | Arg | Gly | Leu | Glu | Trp | Val |
| | | 35 | | | | | 40 | | | | | 45 | | | |
| Ala | Met | Ile | Ser | Ser | Gly | Gly | Ser | Tyr | Thr | Tyr | Tyr | Ala | Asp | Ser | Val |
| | 50 | | | | | 55 | | | | | 60 | | | | |
| Lys | Gly | Arg | Val | Thr | Met | Leu | Arg | Asp | Thr | Ser | Lys | Asn | Gln | Phe | Ser |
| 65 | | | | | 70 | | | | | 75 | | | | | 80 |
| Leu | Arg | Leu | Ser | Ser | Val | Thr | Ala | Ala | Asp | Thr | Ala | Ile | Tyr | Ile | Cys |
| | | | | 85 | | | | | 90 | | | | | 95 | |
| Ala | Arg | His | Gly | Asp | Asp | Pro | Ala | Trp | Phe | Ala | Tyr | Trp | Gly | Gln | Gly |
| | | | | 100 | | | | | 105 | | | | | 110 | |
| Ser | Leu | Val | Thr | Val | Ser | Ser | | | | | | | | | |
| | | | 115 | | | | | | | | | | | | |

( 2 ) INFORMATION FOR SEQ ID NO:21:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

| Gln | Val | Gln | Leu | Gln | Glu | Ser | Gly | Pro | Gly | Leu | Val | Arg | Pro | Ser | Gln |
|---|---|---|---|---|---|---|---|---|---|---|---|---|---|---|---|
| 1 | | | | 5 | | | | | 10 | | | | | 15 | |
| Thr | Leu | Ser | Leu | Thr | Cys | Thr | Ala | Ser | Gly | Phe | Thr | Phe | Ser | Gly | Tyr |
| | | | 20 | | | | | 25 | | | | | 30 | | |
| Gly | Leu | Ser | Trp | Val | Arg | Gln | Pro | Pro | Gly | Arg | Gly | Leu | Glu | Trp | Val |
| | | 35 | | | | | 40 | | | | | 45 | | | |
| Ala | Met | Ile | Ser | Ser | Gly | Gly | Ser | Tyr | Thr | Tyr | Tyr | Ala | Asp | Ser | Val |
| | 50 | | | | | 55 | | | | | 60 | | | | |
| Lys | Gly | Arg | Val | Thr | Met | Leu | Arg | Asp | Thr | Ser | Lys | Asn | Ser | Leu | Phe |
| 65 | | | | | 70 | | | | | 75 | | | | | 80 |
| Leu | Arg | Leu | Ser | Ser | Val | Thr | Ala | Ala | Asp | Thr | Ala | Val | Tyr | Tyr | Cys |
| | | | | 85 | | | | | 90 | | | | | 95 | |
| Ala | Arg | His | Gly | Asp | Asp | Pro | Ala | Trp | Phe | Ala | Tyr | Trp | Gly | Gln | Gly |
| | | | | 100 | | | | | 105 | | | | | 110 | |
| Thr | Thr | Val | Thr | Val | Ser | Ser | | | | | | | | | |
| | | | 115 | | | | | | | | | | | | |

( 2 ) INFORMATION FOR SEQ ID NO:22:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:22:

| Glu | Val | Gln | Leu | Val | Glu | Ser | Gly | Gly | Gly | Val | Val | Gln | Pro | Gly | Arg |
|---|---|---|---|---|---|---|---|---|---|---|---|---|---|---|---|
| 1 | | | | 5 | | | | | 10 | | | | | 15 | |

|     |     | 5   |     |     |     |     | 10  |     |     |     |     | 15  |     |
| --- | --- | --- | --- | --- | --- | --- | --- | --- | --- | --- | --- | --- | --- |

Ser Leu Arg Leu Ser Cys Ser Ala Ser Gly Phe Thr Phe Ser Gly Tyr
           20                  25                  30

Gly Leu Ser Trp Val Arg Gln Ala Pro Gly Lys Gly Leu Glu Trp Val
           35                  40                  45

Ala Met Ile Ser Ser Gly Gly Ser Tyr Thr Tyr Tyr Ala Asp Ser Val
     50              55                  60

Lys Gly Arg Phe Ala Ile Ser Arg Asp Asn Ala Lys Asn Thr Leu Phe
65                   70                  75                  80

Leu Gln Met Asp Ser Leu Arg Pro Glu Asp Thr Gly Val Tyr Phe Cys
               85                  90                  95

Ala Arg His Gly Asp Asp Pro Ala Trp Phe Ala Tyr Trp Gly Gln Gly
           100                 105                 110

Thr Pro Val Thr Val Ser Ser
           115

(2) INFORMATION FOR SEQ ID NO:23:

(i) SEQUENCE CHARACTERISTICS:
      (A) LENGTH: 110 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:23:

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
           20                  25                  30

Asn Leu His Trp Tyr Gln Gln Lys Pro Gly Lys Ala Pro Lys Leu Leu
           35                  40                  45

Ile Tyr Gly Thr Ser Asn Leu Ala Ser Gly Val Pro Ser Arg Phe Ser
     50              55                  60

Gly Ser Gly Ser Gly Thr Asp Phe Thr Phe Thr Ile Ser Ser Leu Gln
65                  70                  75                  80

Pro Glu Asp Ile Ala Thr Tyr Tyr Cys Gln Gln Trp Ser Ser Tyr Pro
               85                  90                  95

Tyr Met Tyr Thr Phe Gly Gln Gly Thr Lys Val Glu Ile Lys
           100                 105                 110

(2) INFORMATION FOR SEQ ID NO:24:

(i) SEQUENCE CHARACTERISTICS:
      (A) LENGTH: 110 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:24:

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
           20                  25                  30

Asn Leu His Trp Tyr Gln Gln Lys Pro Gly Lys Ala Pro Lys Leu Leu
           35                  40                  45

Ile Tyr Gly Thr Ser Asn Leu Ala Ser Gly Val Pro Ser Arg Phe Ser

```
                50                          55                          60
Gly  Ser  Gly  Ser  Gly  Thr  Asp  Tyr  Thr  Phe  Thr  Ile  Ser  Ser  Leu  Gln
65                       70                       75                       80

Pro  Glu  Asp  Ile  Ala  Thr  Tyr  Tyr  Cys  Gln  Gln  Trp  Ser  Ser  Tyr  Pro
                    85                       90                       95

Tyr  Met  Tyr  Thr  Phe  Gly  Gln  Gly  Thr  Lys  Val  Glu  Ile  Lys
               100                      105                      110
```

( 2 ) INFORMATION FOR SEQ ID NO:25:

( i ) SEQUENCE CHARACTERISTICS:
        ( A ) LENGTH: 110 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:25:

```
Asp  Ile  Gln  Leu  Thr  Gln  Ser  Pro  Ser  Ser  Leu  Ser  Ala  Ser  Val  Gly
1                   5                        10                       15

Asp  Arg  Val  Thr  Ile  Thr  Cys  Ser  Val  Ser  Ser  Ile  Ser  Ser  Asn
               20                       25                       30

Asn  Leu  His  Trp  Tyr  Gln  Gln  Lys  Pro  Gly  Lys  Ala  Pro  Lys  Pro  Trp
          35                       40                       45

Ile  Tyr  Gly  Thr  Ser  Asn  Leu  Ala  Ser  Gly  Val  Pro  Ser  Arg  Phe  Ser
     50                       55                       60

Gly  Ser  Gly  Ser  Gly  Thr  Asp  Phe  Thr  Phe  Thr  Ile  Ser  Ser  Leu  Gln
65                       70                       75                       80

Pro  Glu  Asp  Ile  Ala  Thr  Tyr  Tyr  Cys  Gln  Gln  Trp  Ser  Ser  Tyr  Pro
                    85                       90                       95

Tyr  Met  Tyr  Thr  Phe  Gly  Gln  Gly  Thr  Lys  Val  Glu  Ile  Lys
               100                      105                      110
```

( 2 ) INFORMATION FOR SEQ ID NO:26:

( i ) SEQUENCE CHARACTERISTICS:
        ( A ) LENGTH: 357 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

```
CAGGTSMARC  TGCAGSAGTC  WGGGGGAGAC  TTGGTGAAGC  CTGGAGGGTC    50

CCTGAAACTC  TCCTGTGCAG  CCTCTGGATT  CACTTTCAGT  GGCTATGGCT   100

TGTCTTGGGT  TCGCCAGACT  CCAGACAAGA  GGCTGGAGTG  GGTCGCAATG   150

ATTAGTAGTG  GTGGTAGTTA  TACCTACTAT  GCAGACAGTG  TGAAGGGGCG   200

ATTCGCCATC  TCCAGAGACA  ATGCCAAGAA  CTCCCTGTTC  CTGCAAATGA   250

GCAGTCTGAA  GTCTGACGAC  ACAGCCATTT  ATATCTGTGC  AAGACATGGG   300

GACGATCCCG  CCTGGTTTGC  TTACTGGGGC  CAAGGGACTC  TAGTCACTGT   350

CTCTGCT                                                      357
```

( 2 ) INFORMATION FOR SEQ ID NO:27:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear (x i) SEQUENCE DESCRIPTION: SEQ ID NO:27:

```
Gln Val Xaa Leu Gln Xaa Ser Gly Gly Asp Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Leu Ser Trp Val Arg Gln Thr Pro Asp Lys Arg Leu Glu Trp Val
        35                  40                  45

Ala Met Ile Ser Ser Gly Gly Ser Tyr Thr Tyr Tyr Ala Asp Ser Val
    50                  55                      60

Lys Gly Arg Phe Ala Ile Ser Arg Asp Asn Ala Lys Asn Ser Leu Phe
65                  70                      75                  80

Leu Gln Met Ser Ser Leu Lys Ser Asp Asp Thr Ala Ile Tyr Ile Cys
                85                  90                  95

Ala Arg His Gly Asp Asp Pro Ala Trp Phe Ala Tyr Trp Gly Gln Gly
            100                 105                 110

Thr Leu Val Thr Val Ser Ala
            115
```

(2) INFORMATION FOR SEQ ID NO:28:

(i) SEQUENCE CHARACTERISTICS:
      (A) LENGTH: 330
      (B) TYPE: nucleic acid
      (C) STRANDEDNESS: single
      (D) TOPOLOGY: linear (x i) SEQUENCE DESCRIPTION: SEQ ID NO:28:

```
GACATTGAGC TCACCCAGTC TCCAGCACTC ATGGCTGCAT CTCCAGGGGA      50

GAAGGTCACC ATCACCTGCA GTGTCAGCTC AAGTATAAGT TCCAACAACT     100

TGCACTGGTA CCAGCAGAAG TCAGAAACCT CCCCCAAACC CTGGATTTAT     150

GGCACATCCA ACCTGGCTTC TGGAGTCCCT CTTCGCTTCA GAGGCTTTGG     200

ATCTGGGACC TCTTATTCTC TCACAATCAG CAGCATGGAG GCTGAAGATG     250

CTGCCACTTA TTACTGTCAA CAGTGGAGTA GTTACCCGTA CATGTACACG     300

TTCGGAGGGG GGACCAAGTT GGAAATAAAA                           330
```

(2) INFORMATION FOR SEQ ID NO:29:

(i) SEQUENCE CHARACTERISTICS:
      (A) LENGTH: 110 amino acids
      (B) TYPE: amino acid
      (C) STRANDEDNESS: single
      (D) TOPOLOGY: linear (x i) SEQUENCE DESCRIPTION: SEQ ID NO:29:

```
Asp Ile Glu Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Asn
            20                  25                  30

Asn Leu His Trp Tyr Gln Gln Lys Ser Glu Thr Ser Pro Lys Pro Trp
        35                  40                  45

Ile Tyr Gly Thr Ser Asn Leu Ala Ser Gly Val Pro Leu Arg Phe Arg
    50                  55                      60

Gly Phe Gly Ser Gly Thr Ser Tyr Ser Leu Thr Ile Ser Ser Met Glu
65                  70                      75                  80

Ala Glu Asp Ala Ala Thr Tyr Tyr Cys Gln Gln Trp Ser Ser Tyr Pro
                85                  90                  95
```

| | | | | | | | | | | | | |
|---|---|---|---|---|---|---|---|---|---|---|---|---|
| Tyr | Met | Tyr | Thr | Phe | Gly | Gly | Gly | Thr | Lys | Leu | Glu | Ile | Lys |
| | | | 100 | | | | | 105 | | | | 110 |